US012679891B2

(12) United States Patent
Jonjic et al.

(10) Patent No.: US 12,679,891 B2
(45) Date of Patent: Jul. 14, 2026

(54) ANTIBODIES TO NKP46 AND CONSTRUCTS THEREOF FOR TREATMENT OF CANCERS AND INFECTIONS

(71) Applicants: YISSUM RESEARCH DEVELOPMENT COMPANY OF THE HEBREW UNIVERSITY OF JERUSALEM LTD., Jerusalem (IL); UNIVERSITY OF RIJEKA FACULTY OF MEDICINE, Rijeka (HR)

(72) Inventors: Stipan Jonjic, Rijeka (HR); Ofer Mandelboim, Shoham (IL); Orit Berhani, Jerusalem (IL); Shira Kahalon, Jerusalem (IL)

(73) Assignees: YISSUM RESEARCH DEVELOPMENT COMPANY OF THE HEBREW UNIVERSITY OF JERUSALEM LTD, Jerusalem (IL); UNIVERSITY OF RIJEKA FACULTY OF MEDICINE, Rijeka (HR)

( * ) Notice: Subject to any disclaimer, the term of this patent is extended or adjusted under 35 U.S.C. 154(b) by 773 days.

(21) Appl. No.: 17/995,651

(22) PCT Filed: Apr. 5, 2021

(86) PCT No.: PCT/IL2021/050381
§ 371 (c)(1),
(2) Date: Oct. 6, 2022

(87) PCT Pub. No.: WO2021/205438
PCT Pub. Date: Oct. 14, 2021

(65) Prior Publication Data
US 2023/0183342 A1      Jun. 15, 2023

Related U.S. Application Data

(60) Provisional application No. 63/005,457, filed on Apr. 6, 2020.

(51) Int. Cl.
| | |
|---|---|
| *C07K 16/28* | (2006.01) |
| *A61K 40/15* | (2025.01) |
| *A61K 40/31* | (2025.01) |
| *A61K 40/42* | (2025.01) |
| *A61P 35/00* | (2006.01) |
| *A61K 39/00* | (2006.01) |

(52) U.S. Cl.
CPC .......... *C07K 16/2803* (2013.01); *A61K 40/15* (2025.01); *A61K 40/31* (2025.01); *A61K 40/42* (2025.01); *A61P 35/00* (2018.01); *A61K 2039/505* (2013.01); *C07K 2317/24* (2013.01); *C07K 2317/31* (2013.01); *C07K 2317/565* (2013.01); *C07K 2317/622* (2013.01); *C07K 2317/76* (2013.01); *C07K 2317/92* (2013.01)

(58) Field of Classification Search
CPC ........... C07K 16/2803; C07K 2317/24; C07K 2317/92; A61P 35/00
See application file for complete search history.

(56) References Cited

U.S. PATENT DOCUMENTS

| | | | |
|---|---|---|---|
| 4,816,567 A | 3/1989 | Cabilly | |
| 4,946,778 A | 8/1990 | Ladner | |
| 5,225,539 A | 7/1993 | Winter | |
| 5,530,101 A | 6/1996 | Queen | |
| 5,585,089 A | 12/1996 | Queen | |
| 5,641,870 A | 6/1997 | Rinderknecht | |
| 5,693,761 A | 12/1997 | Queen | |
| 5,693,762 A | 12/1997 | Queen | |
| 10,113,003 B2 * | 10/2018 | Gauthier ............ | A61K 40/4211 |
| 2018/0207290 A1 | 7/2018 | Mandelboim | |

FOREIGN PATENT DOCUMENTS

| | | | | |
|---|---|---|---|---|
| EP | 0404097 A2 | 12/1990 | | |
| JP | 2018524326 A | 8/2018 | | |
| JP | 2019503713 A | 2/2019 | | |
| WO | 8601533 A1 | 3/1986 | | |
| WO | 9007861 A1 | 7/1990 | | |
| WO | 9222653 A1 | 12/1992 | | |
| WO | 9311161 A1 | 6/1993 | | |
| WO | 9315210 A1 | 8/1993 | | |
| WO | 9613583 A2 | 5/1996 | | |
| WO | 9637621 A2 | 11/1996 | | |
| WO | WO-2015197593 A1 * | 12/2015 | .............. | A61P 37/02 |
| WO | WO-2017114694 A1 * | 7/2017 | .............. | A61P 35/00 |
| WO | 2018047154 A1 | 3/2018 | | |

OTHER PUBLICATIONS

Sela-Culang et al. 2013 (The structural basis of antibody-antigen recognition; Frontiers in Immunology 4(302):1-13) (Year: 2013).*
Goel et al. 2004 (Plasticity within the Antigen Combining Site May Manifest as Molecular Mimicry in the Humoral Immune Response ; The Journal of Immunology 173(12):7358-7367 (Year: 2004).*
Lloyd et al. 2009 (Modelling the human immune response: performance of a 1011 human antibody repertoire against a broad panel of therapeutically relevant antigens. Protein Engineering, Design & Selection 22(3):159-168) (Year: 2009).*
Edwards et al. 2003 (The remarkable flexibility of the human antibody repertoire; isolation of over one thousand different antibodies to a single protein, BlyS. Journal of Molecular Biology 334: 103-118) (Year: 2003).*

(Continued)

*Primary Examiner* — Mary Maille Lyons
(74) *Attorney, Agent, or Firm* — Ballard Spahr LLP

(57) ABSTRACT

The present invention provides monoclonal antibodies that recognize human NKp46 with high affinity and specificity and do not block NKp46 binding to its natural ligands. The present invention further provides multi-specific antibodies, chimeric antigen receptors (CAR) and uses thereof in treating diseases, particularly malignancies and infections.

18 Claims, 6 Drawing Sheets
Specification includes a Sequence Listing.

(56) References Cited

OTHER PUBLICATIONS

Arnon et al., (2004) The mechanisms controlling the recognition of tumor- and virus-infected cells by NKp46. Blood 103(2): 664-672.

Berhani et al., (2019) Human anti-NKp46 antibody for studies of NKp46-dependent NK cell function and its applications for type 1 diabetes and cancer research. Eur J Immunol 49(2): 228-241.

Bird et al., (1988) Single-chain antigen-binding proteins. Science 242(4877): 423-426.

Bradbury et al., (2018) When monoclonal antibodies are not monospecific: Hybridomas frequently express additional functional variable regions. MAbs 10(4): 539-546.

Brennan et al., (1985) Preparation of bispecific antibodies by chemical recombination of monoclonal immunoglobulin G1 fragments. Science 229(4708): 81-83.

Carter et al., (1992) High level *Escherichia coli* expression and production of a bivalent humanized antibody fragment. Biotechnology (N Y) 10(2): 163-167.

Clackson et al., (1991) Making antibody fragments using phage display libraries. Nature 352(6336): 624-628.

Fields et al., (2013) Creation of recombinant antigen-binding molecules derived from hybridomas secreting specific antibodies. Nat Protoc 8(6): 1125-1148.

Holliger et al., (1993) "Diabodies": small bivalent and bispecific antibody fragments. Proc Natl Acad Sci U S A 90(14): 6444-6448.

Huston et al., (1988) Protein engineering of antibody binding sites: recovery of specific activity in an anti-digoxin single-chain Fv analogue produced in *Escherichia coli*. Proc Natl Acad Sci U S A 85(16): 5879-5883.

Köhler and Milstein (1975) Continuous cultures of fused cells secreting antibody of predefined specificity. Nature 256 (5517): 495-497.

Lefranc et al., (2003) IMGT unique numbering for immunoglobulin and T cell receptor variable domains and Ig superfamily V-like domains. Dev Comp Immunol 27(1): 55-77.

Mandelboim et al., (2001) Recognition of haemagglutinins on virus-infected cells by NKp46 activates lysis by human NK cells. Nature 409(6823): 1055-1060.

Marks et al., (1991) By-passing immunization. Human antibodies from V-gene libraries displayed on phage. J Mol Biol 222(3): 581-597.

Morimoto and Inouye (1992) Single-step purification of F(ab')2 fragments of mouse monoclonal antibodies (immunoglobulins G1) by hydrophobic interaction high performance liquid chromatography using TSKgel Phenyl-5PW. J Biochem Biophys Methods 24(1-2): 107-117.

Morrison et al., (1984) Chimeric human antibody molecules: mouse antigen-binding domains with human constant region domains. Proc Natl Acad Sci U S A 81(21): 6851-6855.

Scarano et al., (2010) Surface plasmon resonance imaging for affinity-based biosensors. Biosens Bioelectron 25(5): 957-966.

Vitenshtein et al., (2016) NK Cell Recognition of Candida glabrata through Binding of NKp46 and NCR1 to Fungal Ligands Epa1, Epa6, and Epa7. Cell Host Microbe 20(4): 527-534.

Ward et al., (1989) Binding activities of a repertoire of single immunoglobulin variable domains secreted from *Escherichia coli*. Nature 341(6242): 544-546.

Wu and Kabat (1970) An analysis of the sequences of the variable regions of Bence Jones proteins and myeloma light chains and their implications for antibody complementarity. J Exp Med 132(2): 211-250.

Zapata et al., (1995) Engineering linear F(ab')2 fragments for efficient production in *Escherichia coli* and enhanced antiproliferative activity. Protein Eng 8(10): 1057-1062.

* cited by examiner

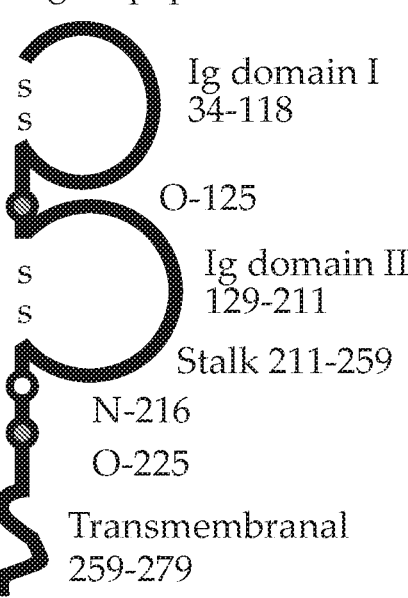
FIGURE 5A
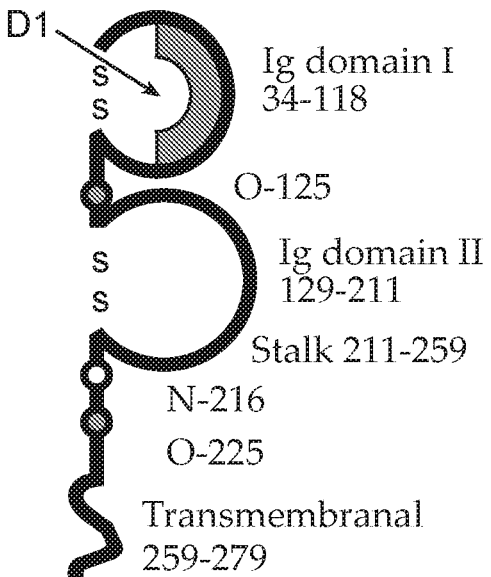
FIGURE 5B
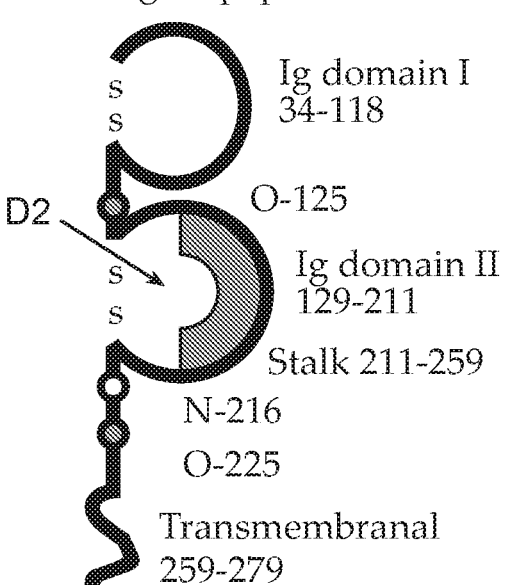
FIGURE 5C
|  | D2-Ig |
|---|---|
| Humanized P4 | 2.48E-16 |
| Humanized K3 | 5.13E-16 |
| P4 | 3.68E-16 |
| K3 | 3.09E-16 |
FIGURE 5D

1

ANTIBODIES TO NKP46 AND CONSTRUCTS THEREOF FOR TREATMENT OF CANCERS AND INFECTIONS

SEQUENCE LISTING

The Sequence Listing submitted herewith is an ASCII text file (2022-10$^{-06}$_Sequence_Listing.txt, created on Oct. 4, 2022, 10521 bytes), is filed via EFS-Web, and is hereby incorporated by reference.

FIELD OF THE INVENTION

The invention is in the field of immunotherapy and relates to antibodies and fragments thereof which bind to the human natural killer receptor NKp46, to polynucleotide sequences encoding these antibodies and fragments, and to cells producing them. The invention further relates to multi-specific and chimeric antigenic receptor constructs of these antibodies and to uses of the antibodies, their fragments and constructs in treating diseases, particularly cancer and acute infections.

BACKGROUND OF THE INVENTION

Cancer immunotherapy is utilized for generating and augmenting an anti-tumor immune response, e.g., by treatment with antibodies specific to antigens on tumor cells, with fusions of antigen presenting cells with tumor cells, or by specific activation of anti-tumor NK or T cells. The ability of recruiting immune cells against tumor cells in a patient provides a therapeutic modality of fighting cancer types and metastasis that so far were considered incurable.

Natural killer (NK) cells are innate effector lymphocytes, that are capable of killing tumor cells and infected cells without prior stimulation. To date, Natural killer (NK) cells have emerged as one of the most crucial first responders to tumor transformation and viral, bacterial, or fungal infections. They are also involved in autoimmune diseases such as type I diabetes and rheumatoid arthritis (RA). NK cells have the distinct ability to recognize many diverse targets due to their numerous germ-line encoded activating and inhibitory receptors. A balance of signals received by these receptors ultimately determines whether the NK cells act against a given target cell, or remain neutral.

Three activating receptors found on NK cells, NKp30, NKp44, and NKp46, are collectively known as Natural Cytotoxicity Receptors (NCRs). These receptors are crucial in NK cells antitumor and antiviral defenses. NKp46 has been established as a critical activating receptor since it is expressed almost exclusively by NK cells. Its ligand repertoire ranges from viral ligands, such as, hemagglutinin (HA) and hemagglutinin-neuraminidase (HN) of influenza virus, Sendai virus, Newcastle disease virus, and poxvirus, to unknown ligands found on bacteria (such as *Fusobacterium nucleatum*), tumors, adipose cells, and human pancreatic beta cells. The identification of the unknown ligands, in particularly the tumor ligands of NKp46, has been intensely investigated for over a decade.

U.S. application No. 20180207290 discloses anti-NKp46 antibodies, toxin conjugates, and therapeutic use of same.

There is an unmet need to provide additional and more effective, specific, safe and/or stable agents that alone, as part of immunologic construct, or in combination with other agents, may potentiate cells of the immune system to attack tumor cells and/or infectious microorganisms.

2

SUMMARY OF THE INVENTION

The present invention provides, in some embodiments, antibodies and fragments thereof that recognize the human NKp46 receptor and are suitable for use in treating cancer and viral diseases. The present invention further provides in some embodiments chimeric antigen receptor (CAR) molecules comprising the binding site of the anti-NKp46 antibodies described herein and methods of their use for adoptive therapy. The present invention further provides in some embodiments, bi- and tri-specific antibodies having specificity to NKp46 and to at least one additional receptor or antigen present on tumor cells or infectious microorganisms.

Advantageously, the anti-NKp46 antibodies disclosed herein are specific to the NKp46 membrane-proximal domain (D2 domain, SEQ ID No: 13) and do not block NKp46 interactions with its ligands. These antibodies do not internalize or degrade the NKp46 receptor and therefore can be used for recruiting NK cells in a variety of therapies. These antibodies and fragment and construct thereof are characterized by having unique sets of CDR sequences, with high specificity and very high affinity to human NKp46. The antibodies are useful in cancer immunotherapy and may also be used for cancer diagnosis. Constructs, such as bi- and multi-specific antibodies, comprising these unique sets of CDR sequences, namely the binding sites of these antibodies, are also useful in treating viral disorders.

According to one aspect, the present invention provides an antibody, or an antibody fragment thereof comprising at least the antigen binding portion, which specifically binds to a sequence in human NKp46 D2 domain and do not block NKp46 interaction with its ligands, said antibody has an affinity to human NKp46 of at least 5×10$^{-9}$M. According to some embodiments, the antibody or antibody fragment has an affinity of at least 10$^{-10}$M.

According to some embodiments, the antibody or antibody fragment comprises a set of six CDR sequences, three CDRs of a heavy-chain (HC) variable region comprising SEQ ID No: 7 and three CDRs of a light-chain (LC) variable region comprising a sequence selected from the group consisting of SEQ ID No: 8 and SEQ ID No: 12, or an analog or derivative thereof having at least 90% sequence identity with said variable region sequence.

There are several methods known in the art for determining the CDR sequences of a given antibody molecule, but there is no standard unequivocal method. Determination of CDR sequences from antibody heavy and light chain variable regions can be made according to any method known in the art, including but not limited to the methods known as KABAT, Chothia and IMGT. A selected set of CDRs may include sequences identified by more than one method, namely, some CDR sequences may be determined using KABAT and some using IMGT, for example. According to some embodiments, the CDR sequences of the mAb variable regions are determined using the IMGT method.

According to some embodiments, the antibody or fragment comprises the CDR sequences of a monoclonal antibody denoted clone K3, namely, the three CDR sequences contained in heavy chain variable region set forth in SEQ ID No: 7 and the three CDR sequences contained in light chain variable region set forth in SEQ ID No: 12, or the CDR sequences of a monoclonal antibody denoted clone P4, namely, the three CDR sequences contained in heavy chain variable region set forth in SEQ ID No: 7 and the three CDR sequences contained in light chain variable region set forth in SEQ ID No: 8.

According to some embodiments, the antibody or the antibody fragment comprises heavy-chain CDR1 comprising the sequence EYSMH (SEQ ID No: 1). According to some embodiments, the antibody or the antibody fragment comprises heavy-chain CDR2 comprising the sequence GISPNSGGTSYNQKFKG (SEQ ID No: 2). According to some embodiments, the antibody or the antibody fragment comprises heavy-chain CDR3 comprising the sequence RDFHSSFDY (SEQ ID No: 3).

According to certain embodiments, the antibody or the antibody fragment comprises: (i) HC CDR1 comprising the sequence EYSMH (SEQ ID No: 1); (ii) HC CDR2 comprising the sequence GISPNSGGTSYNQKFKG (SEQ ID No: 2); and (iii) HC CDR3 comprising the sequence RDFHSSFDY (SEQ ID No: 3).

According to some embodiments, the antibody or the antibody fragment comprises light-chain CDR1 comprising the sequence RASQSISDYLH (SEQ ID No: 4). According to some embodiments, the antibody or the antibody fragment comprises light-chain CDR2 comprising the sequence YASQSIS (SEQ ID No: 5). According to some embodiments, the antibody or the antibody fragment comprises light-chain CDR3 comprising the sequence QNGHSFPLT (SEQ ID No: 6).

According to certain embodiments, the antibody or the antibody fragment comprises: (i) LC CDR1 comprising the sequence RASQSISDYLH (SEQ ID No: 4); (ii) LC CDR2 comprising the sequence YASQSIS (SEQ ID No: 5); and (iii) HC CDR3 comprising the sequence QNGHSFPLT (SEQ ID No: 6).

According to some specific embodiments the antibody or fragment comprises heavy chain CDR1 sequence comprising the sequence EYSMH (SEQ ID No: 1), heavy chain CDR2 comprising the sequence GISPNSGGTSYNQKFKG (SEQ ID No: 2), heavy chain CDR3 comprising the sequence RDFHSSFDY (SEQ ID No: 3), light chain CDR1 comprising the sequence RASQSISDYLH (SEQ ID No: 4), light chain CDR2 comprising the sequence YASQSIS (SEQ ID No: 5), and light chain CDR3 comprising the sequence QNGHSFPLT (SEQ ID No: 6), or analogs thereof comprising no more than 5% amino acid substitution, deletion and/or insertion in the hypervariable region (HVR) sequence.

According to some specific embodiments the antibody or fragment comprises a set of six CDR sequences consisting of:

i. heavy chain CDR1 having a sequence set forth in SEQ ID No: 1;

ii. heavy chain CDR2 having a sequence set forth in SEQ ID No: 2;

iii. heavy chain CDR3 having a sequence set forth in SEQ ID No: 3;

iv. light chain CDR1 having a sequence set forth in SEQ ID No: 4;

v. light chain CDR2 having a sequence set forth in SEQ ID No: 5; and vi. light chain CDR3 having a sequence set forth in SEQ ID No: 6.

According to some embodiments, the antibody or fragment thereof comprises heavy chain variable region set forth in SEQ ID No: 7, or an analog or derivative thereof having at least 90% sequence identity with the heavy chain variable region sequence.

According to some embodiments, the antibody or fragment thereof comprises light chain variable region set forth in SEQ ID No: 8, or an analog thereof having at least 90% sequence identity with the light chain variable region sequence.

According to some embodiments, the antibody or fragment thereof comprises light chain variable region set forth in SEQ ID No: 12, or an analog thereof having at least 90% sequence identity with the light chain variable region sequence.

According to a specific embodiment, the antibody or fragment thereof comprises a heavy chain variable region having a sequence set forth in SEQ ID No: 7, and a light chain variable region having a sequence set forth in SEQ ID No: 8, or an analog thereof having at least 90% sequence identity with the light and/or heavy chain sequence.

According to a specific embodiment, the antibody or fragment thereof comprises a heavy chain variable region having a sequence set forth in SEQ ID No: 7, and a light chain variable region having a sequence set forth in SEQ ID No: 12, or an analog thereof having at least 90% sequence identity with the light and/or heavy chain sequence.

According to a specific embodiment, the antibody or fragment thereof comprises a heavy chain variable region having a sequence set forth in SEQ ID No: 7, and two different light chain variable regions having the sequence set forth in SEQ ID No: 8 and SEQ ID No: 12, or an analog thereof having at least 90% sequence identity with the light and/or heavy chain sequence.

According to some embodiments, the antibody is an isolated monoclonal antibody.

According to some embodiments, the antibody or fragment thereof recognizes human NKp46 with an affinity of at least $5 \times 10^{-9}$M. According to other embodiments, the antibody or antibody fragment binds with an affinity of at least $10^{-9}$M, $5 \times 10^{-10}$M, $10^{-10}$M, $5 \times 10^{-11}$M, $10^{-11}$M, $10^{-12}$M, $10^{-13}$M or even higher to human NKp46. According to some embodiments, the antibody or antibody fragment binds to human NKp46 with affinity at the range of $10^{-9}$M to $10^{-14}$M. According to some embodiments, the antibody or antibody fragment binds to human NKp46 with affinity at the range of $10^{-9}$M to $10^{-10}$M. According to some embodiments, the antibody or antibody fragment binds to human NKp46 with affinity at the range of $10^{-10}$M to $10^{-11}$M. According to some embodiments, the antibody or antibody fragment binds to human NKp46 with affinity at the range of $10^{-11}$M to $10^{-16}$M. According to some embodiments, the antibody or antibody fragment binds to human NKp46 with affinity higher than $10^{-11}$M. According to some embodiments, the antibody or antibody fragment binds to human NKp46 with affinity higher than $10^{-12}$M. Each possibility represents a separate embodiment of the invention.

According to some embodiments, the antibody or fragment thereof recognizes the D2 domain of human NKp46 (SEQ ID No: 13) with an affinity of at least $5 \times 10^{-11}$M. According to some embodiments, the antibody or fragment thereof recognizes the D2 domain of human NKp46 with an affinity of at least $5 \times 10^{-13}$M. According to some embodiments, the antibody or fragment thereof recognizes the D2 domain of human NKp46 with an affinity of at least $5 \times 10^{-1}$+M. According to some embodiments, the antibody or fragment thereof recognizes the D2 domain of human NKp46 with an affinity of at least $5 \times 10^{-15}$M. According to some embodiments, the antibody or antibody fragment recognizes the D2 domain of human NKp46 with affinity at the range of $10^{-13}$M to $10^{-16}$M.

Analogs and derivatives of the isolated antibody and the fragments described above, are also within the scope of the invention.

According to some embodiments, the antibody or antibody fragment analog have at least 90% sequence identity with the hypervariable region of the reference antibody sequence.

According to certain embodiments, the analog or derivative of the isolated antibody or fragment thereof has at least 91, 92, 93, 94, 95, 96, 97, 98 or 99% sequence identity with a variable region of the reference antibody sequence. Each possibility represents a separate embodiment of the invention.

According to some embodiments, the antibody or antibody fragment according to the invention comprises a heavy chain variable region set forth in SEQ ID No: 7, or an analog having at least 95% sequence similarity with said sequence.

According to some embodiments, the antibody or antibody fragment comprises a light chain variable region set forth in SEQ ID No: 8 and/or SEQ ID No: 12, or an analog having at least 95% sequence similarity with said sequence.

According to some embodiments, the antibody or antibody fragment comprises a heavy chain and a light chain, wherein the heavy chain comprises SEQ ID No: 7 and the light chain comprises SEQ ID No: 8 or SEQ ID No: 12. Analogs of the antibodies or fragments, having at least 95% sequence similarity with said heavy or light chains are also included.

According to some embodiments, the analog has at least 96, 97, 98 or 99% sequence similarity or identity with an antibody light or heavy chain variable regions described above. According to some embodiments, the analog comprises no more than one amino acid substitution, deletion or addition to one or more CDR sequences of the hypervariable region, namely, any one of the CDR sequences set forth in SEQ ID Nos: 1, 2, 3, 4, 5, and 6. Each possibility represents a separate embodiment of the present invention. According to some embodiments, the amino acid substitution is a conservative substitution.

According to some embodiments, the antibody or antibody fragment comprises a hypervariable region (HVR) having light and heavy chain regions defined above, in which 1, 2, 3, 4, or 5 amino acids were substituted, deleted and/or added. Each possibility represents a separate embodiment of the invention.

According to some embodiments, the antibody or antibody fragment comprises an HVR having light and heavy chain regions defined above, in which one amino acid was substituted. According to specific embodiments, the antibody or antibody fragment comprises a CDR as defined above, in which one amino acid was substituted.

According to a specific embodiment, the antibody is selected from the group consisting of: chimeric antibody and an antibody fragment comprising at least the antigen-binding portion of an antibody. According to specific embodiments, the antibody is a chimeric antibody. According to yet other embodiments, the chimeric antibody comprised human constant region. According to a specific embodiment, the antibody fragment is selected from the group consisting of: Fab, Fab', F(ab')$_2$, Fd, Fd', Fv, dAb, isolated CDR region, single chain variable region (scFv), single chain antibody (scab), "diabodies", and "linear antibodies". Each possibility represents a separate embodiment of the present invention.

According to some embodiments, the antibody or antibody fragment comprises a constant region selected from the group consisting of: mouse IgG1, mouse IgG2a, mouse IgG2b, mouse IgG3, human IgG1, human IgG2, human IgG3 and human IgG4. Each possibility represents a separate embodiment of the present invention.

According to some specific embodiments, the monoclonal antibody is a chimeric monoclonal antibody.

According to some embodiments, the chimeric antibody comprises human-derived constant regions.

According to some embodiments the human constant regions of the chimeric antibody are selected from the group consisting of: human IgG1, human IgG2, human IgG3, and human IgG4.

According to some embodiments the human constant region of the chimeric antibody is selected from the group consisting of: human IgG1 and human IgG2.

The present invention also provides humanized mAbs comprising a set of six CDRs of any of the mAbs described herein.

According to some embodiments, the humanized antibody or the antibody fragment comprises a set of six CDRs wherein: heavy chain CDR1 sequence comprising the sequence EYSMH (SEQ ID No: 1), heavy chain CDR2 comprising the sequence GISPNSGGTSYNQKFKG (SEQ ID No: 2), heavy chain CDR3 comprising the sequence RDFHSSFDY (SEQ ID No: 3), light chain CDR1 comprising the sequence RASQSISDYLH (SEQ ID No: 4), light chain CDR2 comprising the sequence YASQSIS (SEQ ID No: 5), and light chain CDR3 comprising the sequence QNGHSFPLT (SEQ ID No: 6), or analogs thereof comprising no more than 5% amino acid substitution, deletion and/or insertion in the hypervariable region (HVR) sequence.

According to some embodiments, the humanized antibody or the antibody fragment comprises a set of six CDR sequences consisting of:

i. heavy chain CDR1 having a sequence set forth in SEQ ID No: 1;

ii. heavy chain CDR2 having a sequence set forth in SEQ ID No: 2;

iii. heavy chain CDR3 having a sequence set forth in SEQ ID No: 3;

iv. light chain CDR1 having a sequence set forth in SEQ ID No: 4;

v. light chain CDR2 having a sequence set forth in SEQ ID No: 5; and vi. light chain CDR3 having a sequence set forth in SEQ ID No: 6.

According to some embodiments, the humanized antibody comprises a heavy chain variable region sequence SEQ ID No: 14, or an analog or derivative thereof having at least 90% sequence identity with the heavy chain variable region sequence.

According to some embodiments, the humanized antibody comprises a light chain variable region sequence selected from the group consisting of SEQ ID No: 15 and SEQ ID No: 16, or an analog or derivative thereof having at least 90% sequence identity with the heavy chain variable region sequence.

According to some embodiments, the humanized antibody comprises a set of a heavy chain and a light chain, wherein said set is selected from the group consisting of:

i. SEQ NOs: 14 and 15; and ii. SEQ NOs: 14 and 16.

According to some embodiments, a conjugate comprising an antibody or antibody fragment thereof as described herein by its six CDR sequences, is provided.

Antibodies or fragments thereof according to the present invention may be attached to a radioactive moiety, or an identifiable moiety.

Polynucleotide sequences encoding antibodies, having high affinity and specificity for human NKp46, as well as vectors and host cells carrying these polynucleotide sequences, are provided according to another aspect of the present invention.

According to some embodiments, polynucleotide sequences encoding the amino acid sequences of heavy chain variable region and light chain variable region described above are provided.

According to some embodiments, the polynucleotide sequence encodes an antibody or antibody fragment or chain capable of binding to an epitope within the human NKp46 protein to which binds: (i) an antibody (herein identified as clone P4) having a heavy chain variable region of SEQ ID No: 7 and a light chain variable region of SEQ ID No: 8; or (ii) an antibody (herein identified as clone K3) having a heavy chain variable region of SEQ ID No: 7 and a light chain variable region of SEQ ID No: 8 and/or SEQ ID No: 12.

According to some embodiments, the polynucleotide sequence encodes an antibody or antibody fragment or chain comprising the sequence set forth in a sequence selected from the group consisting of: (i) SEQ ID No: 7 and SEQ ID No: 8; and (ii) SEQ ID No: 7 and SEQ ID No: 12. Each possibility represents a separate embodiment of the present invention.

According to yet some embodiments, the polynucleotide sequence according to the invention encodes an antibody or antibody fragment or a chain thereof comprising a set of six CDRs wherein: HC CDR1 is EYSMH (SEQ ID No: 1); HC CDR2 is GISPNSGGTSYNQKFKG (SEQ ID No: 2); HC CDR3 is RDFHSSFDY (SEQ ID No: 3); LC CDR1 is RASQSISDYLH (SEQ ID No: 4); LC CDR2 is YASQSIS (SEQ ID No: 5); and LC CDR3 is QNGHSFPLT (SEQ ID No: 6).

According to some embodiments, the polynucleotide sequences defined above encode at least one antibody chain or antibody fragment comprising at least an antigen-binding portion.

According to some embodiments, the polynucleotide sequence encodes a monoclonal antibody heavy chain variable region comprising a sequence set forth in SEQ ID No: 7 or a variant thereof having at least 90% sequence identity.

According to some embodiments, the polynucleotide sequence encodes a monoclonal antibody light chain variable region comprising a sequence set forth in SEQ ID No: 8 or a variant thereof having at least 90% sequence identity.

According to some embodiments, the polynucleotide sequence encodes a monoclonal antibody light chain variable region comprising a sequence set forth in SEQ ID No: 12, or a variant thereof having at least 90% sequence identity.

According to certain embodiments, the antibody is a monoclonal antibody having two different light chains. According to certain embodiments, the antibody is a monoclonal antibody having the light chains set forth in SEQ ID No: 8 and SEQ ID No: 12.

The present invention provides, according to some embodiments, a polypeptide comprising at least one sequence encoded by at least one polynucleotide sequence disclosed above.

In a further aspect, the present invention provides a nucleic acid construct comprising a nucleic acid molecule encoding at least one antibody chain or fragment thereof according to the present invention. According to some embodiments the nucleic acid construct is a plasmid.

According to some embodiments the plasmid comprises at least one polynucleotide sequence set forth in a sequence selected from the group consisting of SEQ ID No: 9, SEQ ID No: 10 and SEQ ID No: 11. Each possibility represents a separate embodiment of the present invention.

In still another aspect the present invention provides a cell capable of producing an antibody or an antibody fragment comprising the specific CDR sequences and/or specific heavy and light chain variable regions defined above.

According to some embodiments, a cell is provided comprising at least one polynucleotide sequence disclosed above.

According to some embodiments, the cell producing the monoclonal antibody is a hybridoma cell.

According to an aspect, the present invention provides a multi-specific binding molecule comprising the binding site of an antibody or antibody fragment as described herein.

According to some embodiments, the multi-specific molecule comprises a binding site comprising a set of six CDRs wherein: HC CDR1 is EYSMH (SEQ ID No: 1); HC CDR2 is GISPNSGGTSYNQKFKG (SEQ ID No: 2); HC CDR3 is RDFHSSFDY (SEQ ID No: 3); LC CDR1 is RASQSIS-DYLH (SEQ ID No: 4); LC CDR2 is YASQSIS (SEQ ID No: 5); and LC CDR3 is QNGHSFPLT (SEQ ID No: 6).

According to some embodiments, the multi-specific molecule further comprises a different binding site to an NKp46 engaging molecule. According to some embodiments, the multi-specific molecule further comprises a binding site to an NK cells engaging molecule. According to some embodiments, the multi-specific binding molecule further comprises a binding site specific to other NK engagers, CD160 or CD16.

According to some embodiments, the multi-specific binding molecule further comprises a binding site specific to a tumor antigen, a viral antigen, a bacterial antigen or a fungal antigen.

According to some embodiments, the multi-specific binding molecule further comprises a binding site specific to a tumor antigen. According to specific embodiments, multi-specific binding molecule further comprises a binding site specific to hematological or solid tumors comprising but not limited to PDL-1, CD38, BCMA or GPC3.

According to additional embodiments, the multi-specific binding molecule further comprises a binding site specific to a viral antigen. According to specific embodiments, the multi-specific binding molecule further comprises a binding site specific to a Spike protein 1. According to specific embodiments, the multi-specific binding molecule further comprises a binding site specific to ACE2.

According to some embodiments, the fungal antigen is selected from the group consisting of Epa1, Epa6, and Epa7.

According to some embodiments, the multi-specific binding molecule is fused or conjugated to a cytokine. According to specific embodiments, the multi-specific binding molecule is fused or conjugated to a cytokine selected from the group consisting of IL-2, IL-8, IL-10, IL-12, IL-15, IL-21, IFN-α, TNF-α, GM-CSF, TGF-β, and VEGF. Each possibility represents a separate embodiment of the invention.

According to some embodiments, the multi-specific molecule is a bi-specific antibody comprising a binding site comprising a set of six CDRs wherein: HC CDR1 is EYSMH (SEQ ID No: 1); HC CDR2 is GISPNSGGTSYN-QKFKG (SEQ ID No: 2); HC CDR3 is RDFHSSFDY (SEQ ID No: 3); LC CDR1 is RASQSISDYLH (SEQ ID No: 4); LC CDR2 is YASQSIS (SEQ ID No: 5); and LC CDR3 is QNGHSFPLT (SEQ ID No: 6).

According to some embodiments, the bi-specific antibody further comprises a binding site specific to a tumor antigen, a viral antigen, a bacterial antigen or a fungal antigen.

According to some embodiments, the bi-specific antibody further comprises a binding site specific to a viral antigen. According to certain embodiments, the viral antigen is of a virus selected from the group consisting of coronavirus, influenza virus, Human Metapneumovirus (HMPV), Human cytomegalovirus (HCMV), Sendai virus, Newcastle disease virus, and poxvirus. Each possibility represents a separate embodiment of the invention.

According to some embodiments, the virus is a mammalian or avian virus.

According to some specific embodiments, the mammalian virus is a human virus.

According to some embodiments, the coronavirus is selected from the group consisting of SARS and MERS viruses. According to specific embodiments, the coronavirus is SARS-CoV-2 (COVID-19).

According to some specific embodiments, the mammalian influenza virus is selected from human influenza virus and swine influenza virus.

According to some embodiments, the multi-specific molecule is a tri-specific antibody further comprising a binding site to an NKp46 engaging molecule. According to some embodiments, the multi-specific molecule is a tri-specific antibody further comprising a binding site to NK engagers. According to some embodiments, the multi-specific molecule is a tri-specific antibody further comprising a binding site to CD160 or CD16.

According to some embodiments, the multi-specific molecule is a tri-specific antibody further comprising a binding site to a tumor, a viral antigen, a bacterial antigen or a fungal antigen.

According to some embodiments, the tri-specific antibody is fused to a cytokine. According to specific embodiments, the tri-specific antibody is fused to IL15.

According to specific embodiments, the tri-specific binding molecule comprising the binding site of (i) an antibody or antibody fragment as described herein; (ii) an antibody or a fragment thereof specific to CD160 or CD16; and (iii) an antibody or a fragment thereof specific to a tumor antigen.

According to some embodiments, the multi-specific binding molecule is a polypeptide or a multimer of polypeptides. According to some embodiments, each polypeptide is independently selected from monospecific, bispecific and tri-specific polypeptides.

According to some embodiments, the tri-specific binding molecule consist of or comprises one or more scFv molecules.

The present invention provides, according to another aspect, a pharmaceutical composition comprising as an active ingredient, at least one antibody, or an antibody fragment thereof, that recognizes human NKp46 D2 domain with high affinity and specificity, and optionally at least one pharmaceutical acceptable excipient, diluent, salt or carrier, wherein said at least one antibody or antibody fragment does not block NKp46 interaction with its ligand.

According to some embodiments, the pharmaceutical composition comprises at least one monoclonal antibody comprising a set of six CDRs wherein: HC CDR1 is EYSMH (SEQ ID No: 1); HC CDR2 is GISPNSGGTSYN-QKFKG (SEQ ID No: 2); HC CDR3 is RDFHSSFDY (SEQ ID No: 3); LC CDR1 is RASQSISDYLH (SEQ ID No: 4); LC CDR2 is YASQSIS (SEQ ID No: 5); and LC CDR3 is QNGHSFPLT (SEQ ID No: 6).

According to some embodiments, the pharmaceutical composition comprises an antibody or fragment thereof comprising a heavy chain variable region set forth in Sequence No: 7.

According to some embodiments, the pharmaceutical composition comprises an antibody or fragment thereof comprising a light chain variable region having a sequence selected from the group consisting of SEQ ID No: 8, SEQ ID No: 12 and both. Each possibility represents a separate embodiment of the invention.

According to a specific embodiment, the pharmaceutical composition comprises an antibody or fragment thereof comprising a heavy chain variable region having the sequence set forth in SEQ ID No: 7 and a light chain variable region having the sequence set forth in SEQ ID No: 8 or SEQ ID No: 12.

Single chain variable region (scFv) molecules of the antibodies of the present invention are also provided. The scFv molecules comprise the antigen binding site of the antibody expressed in one polypeptide chain. According to some embodiments, the invention provides scFv molecules comprising a heavy chain and a light chain variable region of the anti-NKp46 antibodies. According to certain embodiments, the scFv comprises a hinge region between the two variable regions.

According to some embodiments, the scFv comprises a NKp46 binding site comprising a set of six CDRs wherein: HC CDR1 is EYSMH (SEQ ID No: 1); HC CDR2 is GISPNSGGTSYNQKFKG (SEQ ID No: 2); HC CDR3 is RDFHSSFDY (SEQ ID No: 3); LC CDR1 is RASQSIS-DYLH (SEQ ID No: 4); LC CDR2 is YASQSIS (SEQ ID No: 5); and LC CDR3 is QNGHSFPLT (SEQ ID No: 6).

According to some embodiments, the scFv comprises a sequence set forth in SEQ ID No: 14, or a variant thereof having at least 90% sequence identity.

According to some embodiments, the scFv comprises a sequence set forth in SEQ ID No: 15, or a variant thereof having at least 90% sequence identity.

According to some embodiments, the scFv comprises a sequence set forth in SEQ ID No: 16, or a variant thereof having at least 90% sequence identity.

According to some embodiments, the scFv comprises sequences set forth in SEQ ID No: 14 and SEQ ID No: 15.

According to some embodiments, the scFv comprises sequences set forth in SEQ ID No: 14 and SEQ ID No: 16.

A chimeric antigen receptor (CAR) comprising an extracellular portion (binding domain), capable of binding to NKp46 is provided according to another aspect of the present invention, the CAR comprises an extracellular portion containing any of the provided antibodies or fragment thereof as described herein.

According to some embodiments, the CAR comprises a NKp46 binding site comprising a set of six CDRs wherein: HC CDR1 is EYSMH (SEQ ID No: 1); HC CDR2 is GISPNSGGTSYNQKFKG (SEQ ID No: 2); HC CDR3 is RDFHSSFDY (SEQ ID No: 3); LC CDR1 is RASQSIS-DYLH (SEQ ID No: 4); LC CDR2 is YASQSIS (SEQ ID No: 5); and LC CDR3 is QNGHSFPLT (SEQ ID No: 6).

According to some embodiments, the CAR comprising a set of six CDRs wherein: HC CDR1 is EYSMH (SEQ ID No: 1); HC CDR2 is GISPNSGGTSYNQKFKG (SEQ ID No: 2); HC CDR3 is RDFHSSFDY (SEQ ID No: 3); LC CDR1 is RASQSISDYLH (SEQ ID No: 4); LC CDR2 is YASQSIS (SEQ ID No: 5); and LC CDR3 is QNGHSFPLT (SEQ ID No: 6); and a transmembrane domain, and an intracellular T cell signaling domain.

According to some embodiments, a lymphocyte engineered to express the CAR described herein is provided.

According to some embodiments, a T cell engineered to express the CAR described herein is provided and denoted CAR-T. According to certain embodiments, an NK cell engineered to express the CAR described herein is provided and denoted CAR-NK.

According to some embodiments, a population of lymphocytes engineered to express the CAR described herein is provided. According to specific embodiments, a population of T-cells or NK-cells engineered to express the CAR described herein is provided.

According to some embodiments, the CAR comprises a single chain variable region (scFv) comprising the heavy chain and light chain variable regions of the antibodies described herein.

According to some embodiments, the CAR comprises at least one protein domain selected from the group consisting of a scFv sequence, a CD8 Stalk domain, a CD28 TM domain, a 41BB domain, and a CD3ζ (CD3Z, Zetta) domain. According to some embodiments, the CAR comprises a scFv domain.

According to some embodiments, the CAR comprises a scFv sequence comprising the NKp46 binding site of the antibodies disclosed herein and at least one domain selected from the group consisting of: CD8 Stalk domain, a CD28 TM domain, a 41BB domain, and a CD3Z domain.

According to an aspect, the present invention provides a method of treating cancer in a subject comprising administering a therapeutically effective amount of at least one lymphocyte comprising the CAR as described herein to said subject.

According to some embodiments, the pharmaceutical composition comprising at least one antibody or an antibody fragment thereof, a CAR, or multi-specific antibody as described herein.

According to some embodiments, the pharmaceutical composition according to the present invention is for use in cancer immunotherapy or in enhancing immune response against a viral infection.

According to some embodiments of the invention, the cancer is a metastatic cancer. According to some embodiments, the pharmaceutical composition according to the present invention is for use in inhibiting formation or distribution of metastases, or reducing the total number of metastases in a subject.

According to some embodiments of the invention, the cancer is selected from the group consisting of a leukemia, a lymphoma, a melanoma, a breast cancer, an ovarian cancer, a pancreatic cancer, a colorectal cancer, a colon cancer, a cervical cancer, a kidney cancer, a lung cancer, a thyroid cancer, a prostate cancer, a brain cancer, a renal cancer, a throat cancer, a laryngeal carcinoma, a bladder cancer, a hepatic cancer, a fibrosarcoma, an endometrial cells cancer, a glioblastoma, sarcoma, and a myeloid. Each possibility represents a separate embodiment of the invention.

According to some embodiments, solid tumors are treated by CAR-T or CAR-NK. According to specific embodiments, solid tumors are treated by CAR-T. According to additional embodiments, hematological cancers are treated with CAR-NK or CAR-T cells. According to specific embodiments, hematological cancers are treated with CAR-NK cells.

According to certain embodiments, the cancer is selected from the group consisting of: melanoma, breast cancer, colorectal cancer, kidney cancer, lung cancer, prostate cancer, and brain cancer. Each possibility represents a separate embodiment of the invention.

According to other embodiments, the cancer is hematologic cancer. According to some embodiments, the pharmaceutical composition is for use in treating cancer, together with human lymphocytes.

According to some embodiments, the human lymphocytes are killer cells selected from the group consisting of: T cells, NK cells and NKT cells. Each possibility represents a separate embodiment of the invention.

According to some embodiments, the killer cells are autologous or allogenic.

According to yet another aspect, the present invention provides a method of treating cancer comprising administering to a subject in need thereof, a therapeutically effective amount of a pharmaceutical composition comprising at least one antibody or an antibody fragment thereof, a CAR, or multi-specific antibody as described herein.

The cancer is as described hereinabove.

According to some embodiments of the invention, the therapeutically effective amount results in a decrease in tumor size or in the number of metastases in the subject.

According to some embodiments, the method of treating cancer comprises administering or performing at least one additional anti-cancer therapy. According to certain embodiments, the additional anticancer therapy is surgery, chemotherapy, radiotherapy, or immunotherapy.

According to some embodiments, the method of treating cancer comprises administration of at least one antibody, antibody fragment thereof, tri-specific binding molecule, CAR or bispecific antibody as described herein and an additional anti-cancer agent. According to some embodiments, the additional anti-cancer agent is selected from the group consisting of: immune-modulator, activated lymphocyte cell, kinase inhibitor and chemotherapeutic agent.

According to other embodiments, the immune-modulator is an antibody, antibody fragment or antibody conjugate that binds to an antigen other than human NKp46.

According to some embodiments, the immune-modulator is an antibody against an immune checkpoint molecule. According to some embodiments, the additional immune modulator is an antibody against an immune checkpoint molecule selected from the group consisting of human programmed cell death protein 1 (PD-1), PD-L1 and PD-L2, carcinoembryonic antigen-related cell adhesion molecule 1 (CEACAM1), lymphocyte activation gene 3 (LAG3), CD137, OX40 (also referred to as CD134), killer cell immunoglobulin-like receptors (KIR), TIGIT, PVR, CTLA-4, NKG2A, GITR, and any other checkpoint molecule or a combination thereof. Each possibility represents a separate embodiment of the invention. According to certain embodiments, the additional immune modulator is an antibody against PD-1. According to some embodiments, the additional immune modulator is an antibody against CTLA-4.

According to some embodiments, the anti-cancer agent is selected from the group consisting of: erbitux, cytarabine, fludarabine, fluorouracil, mercaptopurine, methotrexate, thioguanine, gemcitabine, vincristine, vinblastine, vinorelbine, carmustine, lomustine, chlorambucil, cyclophosphamide, cisplatin, carboplatin, ifosfamide, mechlorethamine, melphalan, thiotepa, dacarbazine, bleomycin, dactinomycin, daunorubicin, doxorubicin, idarubicin, mitomycin, mitoxantrone, plicamycin, etoposide, teniposide and any combination thereof. Each possibility represents a separate embodiment of the invention.

According to some embodiments, the anti-cancer agent is epidermal growth factor receptor (EGFR) inhibitor. According to some embodiments, the EGFR inhibitor is selected from the group consisting of: Cetuximab (Erbitux®), Panitumumab (Vectibix®), and necitumumab (Portrazza®). Each possibility represents a separate embodiment of the invention According to some embodiments of the invention, the subject is a human subject.

According to some embodiments of the invention, the use further comprises the use of an agent that downregulates the activity or expression of an immune co-inhibitory receptor.

According to some embodiments of the invention, the immune co-inhibitory receptor is selected from the group consisting of PD-1, TIGIT, PVR, CTLA-4, LAG3, TIM3, BTLA, VISTA, B7H4, CD96, BY55 (CD 160), LAIR1, SIGLEC10, and 2B4. Each possibility represents a separate embodiment of the invention.

According to some embodiments, the method of treating cancer involves preventing or reducing formation, growth or spread of metastases in a subject.

According to an additional aspect, the present invention provides a method of treating an infection in a subject in need thereof, the method comprises administering to the subject a therapeutically effective amount of a pharmaceutical composition comprising at least one antibody, antibody fragment thereof, multi-specific binding molecule, or CAR as described herein. Each possibility represents a separate embodiment of the invention.

According to some embodiments, the infection is selected from the group consisting of a viral infection, a bacterial infection, and a fungal infection.

According to certain embodiments, the viral infection is of a virus selected from the group consisting of coronavirus, influenza virus, Human Metapneumovirus (HMPV), Human cytomegalovirus (HCMV), Sendai virus, Newcastle disease virus, and poxvirus. Each possibility represents a separate embodiment of the invention.

According to some embodiments, the viral infection is caused by a mammalian or avian virus.

According to some specific embodiments, the mammalian virus is a human virus.

According to some embodiments, the coronavirus is selected from the group consisting of: SARS, MERS, and COVID-19.

According to some specific embodiments, the mammalian influenza virus is selected from human influenza virus and swine influenza virus.

According to an aspect, the present invention provides a method of diagnosing or prognosing cancer in a subject, the method comprises determining the expression level of NKp46 in a biological sample of said subject using at least one antibody as described herein.

The present invention further comprises, according to another aspect, a method of determining or quantifying NKp46 in a sample, the method comprising contacting a biological sample with an antibody or antibody fragment, and measuring the level of complex formation, wherein the antibody or antibody fragment comprises a set of six CDRs wherein: HC CDR1 is EYSMH (SEQ ID No: 1); HC CDR2 is GISPNSGGTSYNQKFKG (SEQ ID No: 2); HC CDR3 is RDFHSSFDY (SEQ ID No: 3); LC CDR1 is RASQSIS-DYLH (SEQ ID No: 4); LC CDR2 is YASQSIS (SEQ ID No: 5); and LC CDR3 is QNGHSFPLT (SEQ ID No: 6).

According to some embodiments, the antibody comprises a set of heavy chain and a light chain, wherein said set is selected from the group consisting of:
  i. SEQ NOs: 14 and 15; and
  ii. SEQ NOs: 14 and 16.
Determining and quantifying methods may be performed in-vitro or ex-vivo according to some embodiments or may be used in diagnosing conditions associated with expression of NKp46. The antibodies according to the present invention may be also used to configure screening methods. For example, an enzyme-linked immunosorbent assay (ELISA), or a radioimmunoassay (RIA), as well as method such as IHC or FACS, can be constructed for measuring levels of secreted or cell-associated polypeptide using the antibodies and methods known in the art.

According to some embodiments, the method for detecting or quantifying the presence of NKp46 expressed on cells or secreted to a biological medium, comprises the steps of:
  i. incubating a sample with an antibody specific to human NKp46 or an antibody fragment thereof comprising at least an antigen-binding portion as described herein; and
  ii. detecting the bound NKp46 using a detectable probe.

According to some embodiments, the method further comprises the steps of:
  iii. comparing the amount of (ii) to a standard curve obtained from a reference sample containing a known amount of NKp46; and
  iv. calculating the amount of the NKp46 in the sample from the standard curve.

According to some particular embodiments the sample is body fluid.

According to some embodiments, the method is performed in-vitro or ex-vivo.

According to some embodiments, the antibody or the antibody fragment used for detection or diagnosis comprises a set of six CDRs wherein: heavy chain CDR1 sequence comprising the sequence EYSMH (SEQ ID No: 1), heavy chain CDR2 comprising the sequence GISPNSGGTSYN-QKFKG (SEQ ID No: 2), heavy chain CDR3 comprising the sequence RDFHSSFDY (SEQ ID No: 3), light chain CDR1 comprising the sequence RASQSISDYLH (SEQ ID No: 4), light chain CDR2 comprising the sequence YASQSIS (SEQ ID No: 5), and light chain CDR3 comprising the sequence QNGHSFPLT (SEQ ID No: 6).

A kit for measuring the expression or presence of NKp46 in biological sample comprising at least one antibody or antibody fragment according to the present invention is also provided. According to some embodiments, the kit comprises an antibody or antibody fragment comprising a set of six CDRs wherein: HC CDR1 is EYSMH (SEQ ID No: 1); HC CDR2 is GISPNSGGTSYNQKFKG (SEQ ID No: 2); HC CDR3 is RDFHSSFDY (SEQ ID No: 3); LC CDR1 is RASQSISDYLH (SEQ ID No: 4); LC CDR2 is YASQSIS (SEQ ID No: 5); and LC CDR3 is QNGHSFPLT (SEQ ID No: 6).

According to an aspect, the present invention provides a kit for diagnosing or staging cancer, the diagnostic kit comprises an antibody or antibody fragment thereof as disclosed herein.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 5A-5D. show the binding affinity of the NKp46 antibodies P4 and K3, and the humanized NKp46 antibodies to NKp46 D2 domain. The structure of the NKp46, D1 domain, and D2 domain is presented in FIGS. 5A-5C, respectively. The affinity values (Kd (M)) to D2 domain are presented in FIG. 5D.

DETAILED DESCRIPTION OF THE INVENTION

Figure 1:
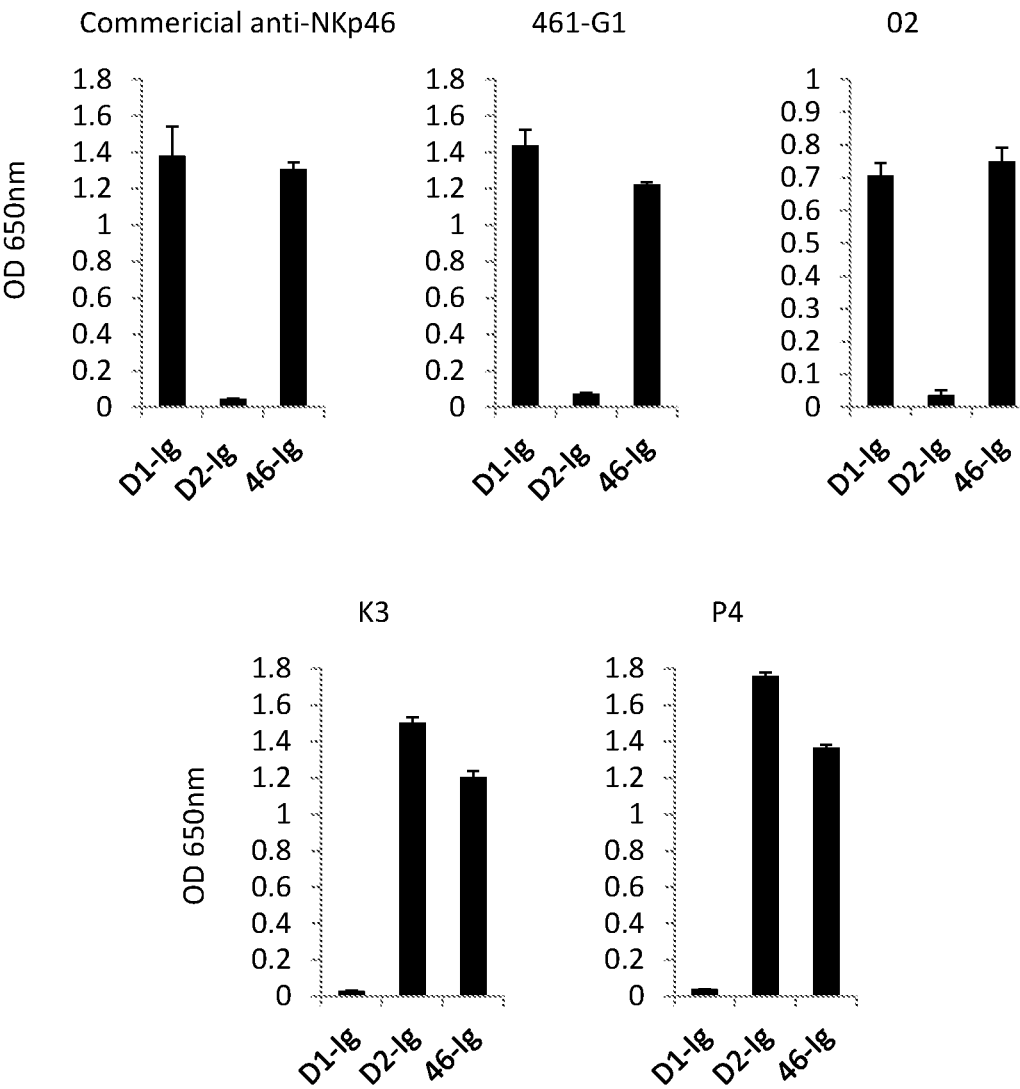
FIG. 1. Identification of the anti-NKp46 mAbs binding sites. The figure shows binding of anti-NKp46 mAbs (commercial anti-NKp46 (9E2), 461-G1, 02, K3, and P4) to NKp46 D1 domain (D1-Ig), NKp46 D2 domain (D2-Ig), or full NKp46 protein-Ig (46-Ig).

The present invention provides antibodies having high affinity and specificity to the human NKp46. The invention also provides multi-specific binding molecules comprising the binding sites of the antibodies as described herein and chimeric antigenic receptors (CAR) comprising the binding site of the novel antibodies. The antibodies by themselves do not affect the NKp46-bearing immune cells and therefore may be used, as part of a construct or multi-specific molecule, in recruiting said immune cells to specific targets such as tumor cells or viral infected cells.

The term "NKp46" as used herein refers to a natural killer protein 46, also known as Natural cytotoxicity triggering receptor 1 (NCR1) or CD335. NKp46 has two Ig-like extracellular domains (D1 and D2) followed by a ~40-residue stalk region, a type I transmembrane domain, and a short cytoplasmic tail. NKp46 is a major NK cell activating receptor that is involved in the elimination of HCV and other viral infected cells and has been shown to regulate interactions of NK cells with other immune cells including T cells and dendritic cells (DC). An exemplary NKp46 according to the invention is set forth in UniPort and GenBank symbols or accession numbers: UniProtKB-O76036 (NCTR1_HUMAN) and Gene ID: 9437. NKp46 has two Ig-like extracellular domains (D1 and D2) followed by a ~40-residue stalk region, a type I transmembrane domain, and a short cytoplasmic tail. D2 domain (or NKp46D2), comprising 134 amino acid residues (corresponding to residues 121-254 of the full-length protein of isoform a). An example for a human D2 domain sequence can be found in SEQ ID No: 13.

The antibodies or fragments thereof according to the invention bind to an epitope in NKp46. Specifically, the antibodies bind to an epitope within the D2 domain of the NKp46 protein.

The term "antibody" is used in the broadest sense and includes monoclonal antibodies (including full length or intact monoclonal antibodies), polyclonal antibodies, multivalent antibodies, and antibody fragments long enough to exhibit the desired biological activity, namely binding to human NKp46.

The term "epitope" or "antigenic determinant" as used herein refers to the region of an antigen molecule that specifically reacts with a particular antibody. Peptide sequences derived from an epitope can be used, alone or in conjunction with a carrier moiety, applying methods known in the art, to immunize animals and to produce additional polyclonal or monoclonal antibodies. Isolated peptides derived from an epitope may be used in diagnostic methods to detect antibodies.

It should be noted that the affinity of an antibody can be quantified using known methods such as, Surface Plasmon Resonance (SPR) (described in Scarano S, Mascini M, Turner A P, Minunni M. Surface plasmon resonance imaging for affinity-based biosensors. Biosens Bioelectron. 2010, 25:957-66), and can be calculated using, e.g., a dissociation constant, Kd, such that a lower Kd reflects higher affinity. Unless otherwise specified, any numerical value for "affinity" in the present disclosure is a dissociation constant.

As used herein, the term "antibody" may refer to any polypeptide or polypeptide complex that includes one or more immunoglobulin-like antigen-binding domains. The term "antibody" may include intact antibodies, such as polyclonal antibodies or monoclonal antibodies (mAbs), multispecific antibodies, as well as proteolytic fragments thereof, such as the Fab or F(ab')2 fragments, single chain antibodies, and complexes thereof.

Immunoglobulins, comprise two heavy chains linked together by disulfide bonds and two light chains, each light chain being linked to a respective heavy chain by disulfide bonds in a "Y" shaped configuration. Proteolytic digestion of an antibody forms Fv (Fragment variable) and Fc (Fragment crystallizable) domains. The antigen binding domains, Fab, include regions where the polypeptide sequence varies. The term F(ab')$_2$ represents two Fab' arms linked together by disulfide bonds. Each heavy chain has at one end a variable domain ($V_H$) followed by a number of constant domains ($C_H$). Each light chain has a variable domain ($V_L$) at one end and a constant domain ($C_L$) at its other end, the light chain variable domain being aligned with the variable domain of the heavy chain and the light chain constant domain being aligned with the first constant domain of the heavy chain (CH1). The variable domains of each pair of light and heavy chains form the antigen-binding site. The domains on the light and heavy chains have the same general structure and each domain comprises four framework regions, whose sequences are relatively conserved, joined by three hypervariable domains known as complementarity determining regions (CDRs 1-3). These domains contribute specificity and affinity of the antigen-binding site.

CDR identification or determination from a given heavy or light chain variable sequence, is typically made using one of few methods known in the art. For example, such determination is made according to the Kabat (Wu T. T and Kabat E. A., *J Exp Med*, 1970; 132:211-50) and IMGT (Lefranc M-P, et al., *Dev Comp Immunol*, 2003, 27:55-77).

When the term "CDR having a sequence", or a similar term is used, it includes options wherein the CDR comprises the specified sequences and also options wherein the CDR consists of the specified sequence.

The antigen specificity of an antibody is based on the hyper variable region (HVR), namely the unique CDR sequences of both light and heavy chains that together form the antigen-binding site.

The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ). Both isotopes are found in all antibody classes.

The present invention further provides chimeric antibody comprising human-derived constant regions, and humanized antibodies specific to the human NKp46. Advantageously, humanized antibodies avoid the risk of adverse immune response towards the antibodies and are therefore safe for in-vivo use in humans.

Antibody Fragments

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 1989, 341, 544-546) which consists of a VH domain; (vii) isolated CDR regions; (viii) F(ab')₂ fragments, a bivalent fragment including two Fab' fragments linked by a disulphide bridge at the hinge region; (ix) single chain antibody molecules (e.g. single chain Fv; scFv) (Bird et al., Science 1988, 242, 423-426; and Huston et al., Proc. Natl. Acad. Sci. (USA) 1988, 85, 5879-5883); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 1993, 90, 6444-6448); (xi) "linear antibodies" comprising a pair of tandem Fd segments (VH-CH1-VH-CH1) which, together with complementary light chain polypeptides, form a pair of antigen binding regions (Zapata et al. Protein Eng., 1995, 8, 1057-1062; and U.S. Pat. No. 5,641,870).

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). However, these fragments can now be produced directly by recombinant host cells. For example, the antibody fragments can be isolated from antibody phage libraries. Alternatively, Fab'-SH fragments can be directly recovered from E. coli and chemically coupled to form F(ab')₂ fragments (Carter et al., Bio/Technology 10:163-167 (1992)). According to another approach, F(ab')₂ fragments can be isolated directly from recombinant host cell culture. Other techniques for the production of antibody fragments will be apparent to the skilled practitioner. In other embodiments, the antibody of choice is a single chain Fv fragment (scFv).

Single chain antibodies can be single chain composite polypeptides having antigen binding capabilities and comprising amino acid sequences homologous or analogous to the variable regions of an immunoglobulin light and heavy chain i.e. linked V$_H$-V$_L$ or single chain Fv (scFv). Techniques for the production of single-chain antibodies (U.S. Pat. No. 4,946,778) can be adapted to produce single-chain antibodies to NKp46.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. mAbs may be obtained by methods known to those skilled in the art. For example, the monoclonal antibodies to be used in accordance with the present invention may be made by the hybridoma method first described by Kohler et al., Nature 1975, 256, 495, or may be made by recombinant DNA methods (see, e.g., U.S. Pat. No. 4,816,567). Monoclonal antibodies may also be isolated from phage antibody libraries using the techniques described, for example, in Clackson et al., Nature 1991, 352, 624-628 or Marks et al., J. Mol. Biol., 1991, 222:581-597.

The design and development of recombinant monovalent antigen-binding molecules derived from monoclonal antibodies through rapid identification and cloning of the functional variable heavy (VH) and variable light (VL) genes and the design and cloning of a synthetic DNA sequence optimized for expression in recombinant bacteria are described in Fields et at. 2013, 8 (6): 1125-48.

The mAbs of the present invention may be of any immunoglobulin class including IgG, IgM, IgE, IgA, and IgD. A hybridoma producing a mAb may be cultivated in-vitro or in-vivo. High titers of mAbs can be obtained by in-vivo production where cells from the individual hybridomas are injected intra-peritoneally into pristine-primed Balb/c mice to produce ascites fluid containing high concentrations of the desired mAbs. mAbs may be purified from such ascites fluids, or from culture supernatants, using methods well known to those of skill in the art.

Anti-idiotype antibodies specifically immunoreactive with the hypervariable regions of an antibody of the invention are also comprehended.

The invention provides a monoclonal antibody or an antibody fragment comprising an antigen binding domain (ABD) which comprises three CDRs of a light chain and three CDRs of a heavy chain, wherein said ABD has at least 90% sequence identity or similarity with an ABD of a monoclonal mouse antibody comprising: (i) a heavy variable chain comprising the amino acid SEQ ID No: 7 and a light variable chain comprising the amino acid SEQ ID No: 8 and/or SEQ ID No: 12. Such antibody may have an ABD domain having at least 93%, at least 94%, at least 95%, at least 96, at least 97, at least 98, at least 99% sequence identity or similarity or 100% sequence identity with corresponding ABD of antibodies clone K3 or clone P4.

Sequence identity is the amount of amino acids or nucleotides which match exactly between two different sequences. Sequence similarity permits conservative substitution of amino acids to be determined as identical amino acids. The polynucleotide sequences described herein may be codon-optimized for expression in specific cells, such as human cells. Codon optimization does not change the encoded amino acid sequences of the antibody's chain but may, for example, increase the expression in cells.

The invention also provides conservative amino acid variants of the antibody molecules according to the invention. Variants according to the invention also may be made that conserve the overall molecular structure of the encoded proteins. Given the properties of the individual amino acids comprising the disclosed protein products, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved. The term "antibody analog" as used herein refers to an antibody derived from another antibody by one or more conservative amino acid substitutions.

The term "antibody variant" as used herein refers to any molecule comprising the antibody of the present invention. For example, fusion proteins in which the antibody or an antigen-binding-fragment thereof is linked to another chemical entity is considered an antibody variant.

Analogs and variants of the antibody sequences are also within the scope of the present application. These include, but are not limited to, conservative and non-conservative substitution, insertion and deletion of amino acids within the sequence. Such modification and the resultant antibody analog or variant are within the scope of the present invention as long as they confer, or even improve the binding of the antibody to the human NKp46.

Conservative substitutions of amino acids as known to those skilled in the art are within the scope of the present invention. Conservative amino acid substitutions include replacement of one amino acid with another having the same type of functional group or side chain, e.g., aliphatic, aromatic, positively charged, negatively charged. These substitutions may enhance oral bioavailability, penetration, and targeting to specific cell populations, immunogenicity, and the like. One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. For example, according to one table known in the art, the following six groups each contain amino acids that are conservative substitutions for one another:

1) Alanine (A), Serine(S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

It should be emphasized that the variant chain sequences are determined by sequencing methods using specific primers. Different sequencing methods employed on the same sequence may result in slightly different sequences due to technical issues and different primers, particularly in the sequence terminals.

The terms "molecule having the antigen-binding portion of an antibody" and "antigen-binding-fragments" as used herein are intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, Fab mini-antibodies (see e.g., WO 93/15210, U.S. patent application Ser. No. 08/256,790, WO 96/13583, U.S. patent application Ser. No. 08/817,788, WO 96/37621, U.S. patent application Ser. No. 08/999,554), and single-chain antibodies incorporating such reactive fraction, as well as any other type of molecule in which such antibody reactive fraction has been physically inserted. Such molecules may be provided by any known technique, including, but not limited to, enzymatic cleavage, peptide synthesis or recombinant techniques.

The antibodies herein specifically include "chimeric" antibodies in which a portion of the heavy and/or light chain is identical with or homologous to corresponding sequences in antibodies derived from a particular species, or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816, 567; and Morrison et al., Proc. Natl. Acad. Sci. USA 81:6851-6855 (1984)). In addition, complementarity determining region (CDR) grafting may be performed to alter certain properties of the antibody molecule including affinity or specificity. A non-limiting example of CDR grafting is disclosed in U.S. Pat. No. 5,225,539.

Chimeric antibodies are molecules of which different portions are derived from different animal species, such as those having a variable region derived from a murine mAb and a human immunoglobulin constant region. Antibodies that have variable region framework residues substantially from human antibody (termed an acceptor antibody) and CDRs substantially from a mouse antibody (termed a donor antibody) are also referred to as humanized antibodies. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (for example PCT patent applications WO 86/01533, WO 97/02671, WO 90/07861, WO 92/22653 and U.S. Pat. Nos. 5,693,762, 5,693,761, 5,585,089, 5,530,101 and 5,225,539).

According to some embodiments, the antibody is a monoclonal antibody.

According to some specific embodiments, the monoclonal antibody is a chimeric monoclonal antibody.

According to some embodiments, the chimeric antibody comprises human-derived constant regions.

According to some embodiments the human constant regions of the chimeric antibody are selected from the group consisting of: human IgG1, human IgG2, human IgG3, and human IgG4.

According to some embodiments the human constant regions of the chimeric antibody are selected from the group consisting of: human IgG1 and human IgG2.

According to a particular embodiment, a chimeric monoclonal antibody which recognizes human NKp46 is provided comprising a set of six CDRs wherein: HC CDR1 is EYSMH (SEQ ID No: 1); HC CDR2 is GISPNSGGTSYN-QKFKG (SEQ ID No: 2); HC CDR3 is RDFHSSFDY (SEQ ID No: 3); LC CDR1 is RASQSISDYLH (SEQ ID No: 4); LC CDR2 is YASQSIS (SEQ ID No: 5); and LC CDR3 is QNGHSFPLT (SEQ ID No: 6).

According to some embodiments, the antibodies are humanized antibodies.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody refers to a variant of the non-human antibody that has undergone humanization, typically to reduce immunogenicity to humans, while retaining the specificity and affinity of the parental non-human antibody. According to some embodiments, some FR residues in a humanized antibody are substituted with corresponding residues from a non-human antibody (e.g., the antibody from which the CDR residues are derived), e.g., to restore or improve antibody specificity or affinity.

A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Pharmacology

In pharmaceutical and medicament formulations, the active agent is preferably utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired exposure.

Typically, the antibodies and fragments of the present invention comprising the antigen binding portion of an antibody or comprising another polypeptide including a peptide-mimetic will be suspended in a sterile saline solution for therapeutic uses. The pharmaceutical compositions may alternatively be formulated to control release of active ingredient (molecule comprising the antigen binding portion of an antibody) or to prolong its presence in a patient's system. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly(ethylene-co-vinyl acetate) and matrices of a polyanhydride copolymer of a stearic acid dimer and sebaric acid. The rate of release of the molecule according to the present invention, i.e., of an antibody or antibody fragment, from such a matrix depends upon the molecular weight of the molecule, the amount of the molecule within the matrix, and the size of dispersed particles.

The pharmaceutical composition of this invention may be administered by any suitable means, such as intravenously, intratumorally, orally, intranasally, subcutaneously, intramuscularly, intra-arterially, intraarticulary, intralesionally or parenterally. Ordinarily, intravenous (i.v.) administration is used for delivering antibodies.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered, its persistence in the blood circulation, and the judgment of the treating physician.

As used herein the term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The cancer amendable for treatment by the present invention includes, but is not limited to: leukemia or lymphoid malignancies, carcinoma, lymphoma, blastoma, and sarcoma. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high-grade immunoblastic NHL; high-grade lymphoblastic NHL; high-grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. According to some embodiments, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. The cancerous conditions amendable for treatment of the invention include metastatic cancers.

According to specific embodiments, the cancer is selected from the group consisting of NK cell leukemia, and large granular lymphocyte (LGL) leukemia.

According to other embodiments, the pharmaceutical composition according to the invention is for use in treating cancer characterized by overexpression of NKp46.

According to additional embodiments, "therapeutically effective amount" refers to an amount of a drug effective to treat a viral disease or disorder in a mammal.

The molecules of the present invention as active ingredients are dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, pH buffering agents.

The pharmaceutical composition according to the present invention may be administered together with an anti-neoplastic composition.

The term "treatment" as used herein refers to both therapeutic treatment and prophylactic or preventative measures. Those in need of treatment include those already with the disorder as well as those in which the disorder is to be prevented.

The term "cancer" refers to or describes the physiological condition in mammals that is typically characterized by unregulated cell growth. Examples of cancer include but are not limited to, leukemia, carcinoma, lymphoma, blastoma, sarcoma, and. More particular examples of such cancers include leukemia, lymphoma, melanoma, lung, thyroid, breast, colon, prostate, hepatic, bladder, renal, cervical, pancreatic, myeloid, ovarian, uterus, sarcoma, biliary, or endometrial cancer.

According to some embodiments, the method of treating cancer comprises administering the pharmaceutical composition as part of a treatment regimen comprising administration of at least one additional anti-cancer agent.

According to some embodiments, the anti-cancer agent is selected from the group consisting of an antimetabolite, a mitotic inhibitor, a taxane, a topoisomerase inhibitor, a topoisomerase II inhibitor, an asparaginase, an alkylating agent, an antitumor antibiotic, and combinations thereof. Each possibility represents a separate embodiment of the invention.

According to some embodiments, the antimetabolite is selected from the group consisting of cytarabine, fludarabine, fluorouracil, mercaptopurine, methotrexate, thioguanine, gemcitabine, and hydroxyurea. According to some embodiments, the mitotic inhibitor is selected from the group consisting of vincristine, vinblastine, and vinorelbine. According to some embodiments, the topoisomerase inhibitor is selected from the group consisting of topotecan and irinotecan. According to some embodiments, the alkylating agent is selected from the group consisting of busulfan, carmustine, lomustine, chlorambucil, cyclophosphamide, cisplatin, carboplatin, ifosfamide, mechlorethamine, melphalan, thiotepa, dacarbazine, and procarbazine. According to some embodiments, the antitumor antibiotic is selected from the group consisting of bleomycin, dactinomycin, daunorubicin, doxorubicin, idarubicin, mitomycin, mitoxantrone, and plicamycin. According to some embodiments, the topoisomerase II is selected from the group consisting of etoposide and teniposide. Each possibility represents a separate embodiment of the present invention.

According to some particular embodiments, the additional anti-cancer agent is selected from the group consisting of bevacizumab, carboplatin, cyclophosphamide, doxorubicin hydrochloride, gemcitabine hydrochloride, topotecan hydrochloride, thiotepa, and combinations thereof. Each possibility represents a separate embodiment of the present invention.

Monoclonal antibodies according to the present invention may be used as part of combined therapy with at least one anti-cancer agent. According to some embodiments, the additional anti-cancer agent is an immuno-modulator, an activated lymphocyte cell, a kinase inhibitor or a chemotherapeutic agent.

According to some embodiments, the anti-cancer agent is an immuno-modulator, whether agonist or antagonist, such as antibody against an immune checkpoint molecule.

Checkpoint immunotherapy blockade has proven to be an exciting new venue of cancer treatment. Immune checkpoint pathways consist of a range of co-stimulatory and inhibitory molecules which work in concert in order to maintain self-tolerance and protect tissues from damage by the immune system under physiological conditions. Tumors take advantage of certain checkpoint pathways in order to evade the immune system. Therefore, the inhibition of such pathways has emerged as a promising anti-cancer treatment strategy.

The anti-cytotoxic T lymphocyte 4 (CTLA-4) antibody ipilimumab (approved in 2011) was the first immunotherapeutic agent that showed a benefit for the treatment of cancer patients. The antibody interferes with inhibitory signals during antigen presentation to T cells. Anti-programmed cell death 1 (PD-1) antibody pembrolizumab (approved in 2014) blocks negative immune regulatory signaling of the PD-1 receptor expressed by T cells. An additional anti-PD-1 agent was filed for regulatory approval in 2014 for the treatment of non-small cell lung cancer (NSCLC). Active research is currently exploring many other immune checkpoints, among them: CEACAM1, NKG2A, B7-H3, B7-H4, VISTA, CD112R, lymphocyte activation gene 3 (LAG3), CD137, OX40 (also referred to as CD134), and killer cell immunoglobulin-like receptors (KIR).

According to some specific embodiments, the immuno-modulator is selected from the group consisting of: an antibody inhibiting CTLA-4, an anti-human programmed cell death protein 1 (PD-1), PD-L1 and PD-L2 antibody, an activated cytotoxic lymphocyte cell, a lymphocyte activating agent, an antibody against CEACAM, an antibody against TIGIT, and a RAF/MEK pathway inhibitor. Each possibility represents a separate embodiment of the present invention. According to some specific embodiments, the additional immuno-modulator is selected from mAb to PD-1, mAb to PD-L1, mAb to PD-L2, mAb to CEACAM1, mAb to CTLA-4, mAB to TIGIT, PVR, Interleukin 2 (IL-2) or lymphokine-activated killer (LAK) cell.

According to other embodiments the additional anti-cancer agent is a chemotherapeutic agent. The chemotherapy agent, which could be administered together with the antibody according to the present invention, or separately, may comprise any such agent known in the art exhibiting anticancer activity, including but not limited to: mitoxantrone, topoisomerase inhibitors, spindle poison from *vinca*: vinblastine, vincristine, vinorelbine (taxol), paclitaxel, docetaxel; alkylating agents: mechlorethamine, chlorambucil, cyclophosphamide, melphalan, ifosfamide; methotrexate; 6-mercaptopurine; 5-fluorouracil, cytarabine, gemcitabine; podophyllotoxins: etoposide, irinotecan, topotecan, dacarbazine; antibiotics: doxorubicin (adriamycin), bleomycin, mitomycin; nitrosoureas: carmustine (BCNU), lomustine, epirubicin, idarubicin, daunorubicin; inorganic ions: cisplatin, carboplatin; interferon, asparaginase; hormones: tamoxifen, leuprolide, flutamide, and megestrol acetate.

According to some embodiments, the chemotherapeutic agent is selected from alkylating agents, antimetabolites, folic acid analogs, pyrimidine analogs, purine analogs and related inhibitors, *vinca* alkaloids, epipodophyllotoxins, antibiotics, L-asparaginase, topoisomerase inhibitor, interferons, platinum coordination complexes, anthracenedione substituted urea, methyl hydrazine derivatives, adrenocortical suppressant, adrenocorticosteroids, progestins, estrogens, antiestrogen, androgens, antiandrogen, and gonadotropin-releasing hormone analog. According to another embodiment, the chemotherapeutic agent is selected from the group consisting of 5-fluorouracil (5-FU), leucovorin (LV), irinotecan, oxaliplatin, capecitabine, paclitaxel and docetaxel. One or more chemotherapeutic agents can be used.

According to some embodiments, the pharmaceutical composition according to the present invention is for use in treating cancer or for use in treating an infection. According to certain embodiments, the infection is a viral infection, a bacterial infection or a fungal infection.

According to some embodiments, a pharmaceutical composition, comprising at least one antibody or fragment thereof according to the present invention, and a pharmaceutical composition, comprising an immuno-modulator or a kinase inhibitor, are used in treatment of cancer by separate administration.

According to still another aspect the present invention provides a method of treating cancer in a subject in need thereof comprising administering to said subject a therapeutically effective amount of a monoclonal antibody or antibody fragment, a CAR molecule, or a multi-specific binding molecule according to the present invention.

The term "effective amount" as used herein refers to a sufficient amount of the monoclonal antibody of the antibody fragment that, when administered to a subject will have the intended therapeutic effect. The effective amount required to achieve the therapeutic end result may depend on a number of factors including, for example, the specific type of the tumor and the severity of the patient's condition, and whether the combination is further co-administered with radiation. The effective amount (dose) of the active agents, in the context of the present invention should be sufficient to affect a beneficial therapeutic response in the subject over time, including but not limited to inhibition of tumor growth, reduction in the rate of tumor growth, prevention of tumor and metastasis growth and enhanced survival.

Toxicity and therapeutic efficacy of the compositions described herein can be determined by standard pharmaceutical procedures in cell cultures or experimental animals, e.g., by determining the IC50 (the concentration which provides 50% inhibition) and the maximal tolerated dose for a subject compound. The data obtained from these cell culture assays, and animal studies can be used in formulating a range of dosages for use in humans. The dosage may vary depending inter alia upon the dosage form employed, the dosing regimen chosen, the composition of the agents used for the treatment and the route of administration utilized, among other relevant factors. The exact formulation, route of administration and dosage can be chosen by the individual physician in view of the patient's condition. Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

The term "administering" or "administration of" a substance, a compound or an agent to a subject can be carried out using one of a variety of methods known to those skilled in the art. For example, a compound or an agent can be administered enterally or parenterally. Enterally refers to administration via the gastrointestinal tract including per os, sublingually or rectally. Parenteral administration includes administration intravenously, intradermally, intramuscularly, intraperitoneally, subcutaneously, ocularly, sublingually, intranasally, by inhalation, intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some embodiments, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

Antibodies are generally administered in the range of about 0.1 to about 20 mg/kg of patient weight, commonly about 0.5 to about 10 mg/kg, and often about 1 to about 5 mg/kg. In this regard, it is preferred to use antibodies having a circulating half-life of at least 12 hours, preferably at least 4 days, more preferably up to 21 days. Chimeric antibodies are expected to have circulatory half-lives of up to 14-21 days. In some cases, it may be advantageous to administer a large loading dose followed by periodic (e.g., weekly) maintenance doses over the treatment period. Antibodies can also be delivered by slow-release delivery systems, pumps, and other known delivery systems for continuous infusion.

The antibodies of the present invention can be used in CAR-based adoptive immunotherapies that utilizes engineered lymphocytes comprising the CAR for treating cancer. CAR-T system is described herein as a non-limiting example.

The T cell therapy utilizes a chimeric antigen receptor (CAR) in the treatment of cancer or tumors (i.e., CAR-T cell therapy). CAR-T cell therapy is a cellular immunotherapy which involves administration to a cancer patient genetically engineered T-cells that act on tumor cells and cause apoptosis of the tumor cells. The genetically engineered T cells are prepared by expressing on a T cell a CAR having variable regions of an antibody (VL and VH) combined with an intracellular domain, such as fragment of a CD3ζ chain sequence, using gene transfer technique. CAR is a general term for a chimeric protein in which a light chain and a heavy chain of a variable region of a monoclonal antibody specific for a tumor antigen are linked to each other, which are then linked to a T-cell receptor (TCR) chain at the C-terminal side.

According to some embodiments, the CAR comprises at least one protein domain selected from the group consisting of a CD8 Stalk domain, a CD28 TM domain, a 41BB domain, and a CD3ζ domain.

According to some embodiments, the CAR comprises a costimulatory domain derived from 4-1BB (or 41BB or CD137), ICOS, OX40, CD27, KIR2DS2, MYD88-CD40, or CD28. In some embodiments, the CAR comprises signaling domains of CD3ζ, 41BB and CD28.

According to some embodiments, the CAR comprises a transmembrane domain (TM) selected from CD28 TM, DAP12 TM, CD8 TM, CD3ζTM, DAP10 TM, and ICOS TM.

According to some embodiments, the CAR comprises a hinge region sequence. According to some embodiments, the hinge region sequence is derived from CD8, CD28, or IgG4 hinge.

According to some embodiments, a chimeric antigen receptor (CAR) comprising the heavy chain variable region (VH) and the light chain variable region (VL) according to the invention is provided. According to certain embodiments, a genetically modified lymphocyte having the CAR being expressed on its surface is provided. According to some specific embodiments, a genetically modified T cell having the CAR being expressed on its surface (CAR-T cell) is provided.

According to some embodiments, the CAR comprises a NKp46 binding site comprising a set of six CDRs wherein: HC CDR1 is EYSMH (SEQ ID No: 1); HC CDR2 is GISPNSGGTSYNQKFKG (SEQ ID No: 2); HC CDR3 is RDFHSSFDY (SEQ ID No: 3); LC CDR1 is RASQSIS-DYLH (SEQ ID No: 4); LC CDR2 is YASQSIS (SEQ ID No: 5); and LC CDR3 is QNGHSFPLT (SEQ ID No: 6), or an analog or derivative thereof having at least 90% sequence identity with said antibody or fragment.

According to some embodiments, the analog or derivative has at least 91%, 92%, 93%, 94%, 95%, 96%, 97%, 98%, or 99% sequence identity with said antibody or fragment sequence.

According to some embodiments, the CAR comprises a NKp46 binding site comprising three complementarity determining regions (CDRs) of a heavy-chain (HC) variable region comprising SEQ ID No: 7 and three CDRs of a light-chain (LC) variable comprising SEQ ID No: 8 or SEQ ID No: 12.

According to some embodiments, the CAR comprises a NKp46 binding site comprising a set of six CDRs wherein: HC CDR1 is EYSMH (SEQ ID No: 1); HC CDR2 is GISPNSGGTSYNQKFKG (SEQ ID No: 2); HC CDR3 is RDFHSSFDY (SEQ ID No: 3); LC CDR1 is RASQSIS-DYLH (SEQ ID No: 4); LC CDR2 is YASQSIS (SEQ ID No: 5); and LC CDR3 is QNGHSFPLT (SEQ ID No: 6).

According to a certain aspect, the present invention provides a cell comprising the CAR described herein. According to some embodiments, the cell expresses or capable of expressing the CAR of the present invention. According to some embodiments, the cell is a lymphocyte. According to some embodiments, the cell is selected from a T cell and a natural killer (NK) cell.

According to some embodiments, the cell, such as T-cell comprises the nucleic acid molecule encoding the CAR of the present invention. According to other embodiments, the cell, such as T-cell comprises the nucleic acid construct comprising nucleic acid molecule encoding the CAR of the present invention. According to a further embodiment, the present invention provides a vector comprising the nucleic acid construct or molecule encoding the CAR of the present invention. According to such embodiments, the T-cell is capable of expressing or expresses the CAR of the present invention.

According to some embodiments, a lymphocyte engineered to express the CAR described herein is provided. According to some embodiments, a T cell engineered to express the CAR described herein is provided.

According to additional embodiments, an NK cell engineered to express the CAR described herein is provided.

The CAR of the present invention comprises a transmembrane domain (TM domain), a costimulatory domain and an activation domain. According to some embodiments, the TM domain is a TM domain of a receptor selected from CD4, CD3ζ, CD28 and CD8, or an analog thereof having at least 85% amino acid identity to the original sequence and/or the costimulatory domain is selected from a costimulatory domain of a protein selected from CD28, 4-1BB, OX40, iCOS, CD27, CD80, and CD70, an analog thereof having at least 85% amino acid identity to the original sequence and any combination thereof, and/or the activation domain is selected from FcRγ and CD3-ζ activation domains. According to some embodiments, the CAR comprises a leading peptide.

According to some embodiments, the present invention provides a cell composition comprising a plurality of cells of the present invention, e.g. CAR displaying cells.

According to an additional aspect, the present invention provides a multi-specific binding molecule comprising the binding site of an antibody or antibody fragment as described herein.

According to some embodiments, the binding site comprises a set of six CDRs wherein: HC CDR1 is EYSMH (SEQ ID No: 1); HC CDR2 is GISPNSGGTSYNQKFKG (SEQ ID No: 2); HC CDR3 is RDFHSSFDY (SEQ ID No: 3); LC CDR1 is RASQSISDYLH (SEQ ID No: 4); LC CDR2 is YASQSIS (SEQ ID No: 5); and LC CDR3 is QNGHSFPLT (SEQ ID No: 6).

According to some embodiments, the multi-specific antibody is a bispecific antibody.

According to certain embodiments, the multi-specific antibody is a tri-specific antibody.

According to some embodiments, the multi-specific antibody further comprises a binding site to an NK cell engager molecule. As used herein, the term "engager" refers to a molecule that can activate or strengthen the activity of an immune cell. According to some embodiments, the multi-specific antibody further comprises a binding site specific to CD160. According to some embodiments, the multi-specific antibody further comprises a binding site specific to CD16.

CD160 is a Natural Killer Cell Receptor and an Immunoglobulin Superfamily Member. It is a 27 kDa glycoprotein that its expression is tightly associated with peripheral blood NK cells and CD8 T lymphocytes with cytolytic effector activity. Aliases names of CD160 include inter alia BY55, NK1, NK28. Exemplified sequence of CD160 can be found in UniProt accession number 095971.

According to additional embodiments, the multi-specific antibody is fused or conjugated to a cytokine.

According to some embodiments, the multi-specific antibody further comprises a binding site specific to an antigen located on a cancer site.

According to additional embodiments, the multi-specific antibody further comprises a binding site specific to a viral antigen. According to additional embodiments, the multi-specific antibody further comprises a binding site specific to a fungal antigen. According to additional embodiments, the multi-specific antibody further comprises a binding site specific to a bacterial antigen.

According to some embodiments, the multi-specific binding molecule is a polypeptide or a multimer of polypeptides.

According to some embodiments, each polypeptide is independently selected from monospecific, bispecific and tri-specific polypeptides.

According to some embodiments, the multi-specific binding molecule consist of or comprise one or more scFv molecules.

For the binding molecule to be at least tri-specific it is sufficient that each binding specificity is represented by exactly one binding site. Accordingly, a tri-specific binding molecule according to the present invention may be a trivalent molecule. It is also possible that the three binding specificities are implemented by a different number of binding sites each. It may be preferred that one binding specificity is represented by more binding sites than the other two or that two binding specificities may be represented by more binding sites than the third one.

According to some embodiments, a set of six CDRs is a preferred implementation of a given binding site. As is well-known in the art, sets of six CDRs contain a first and a second set, each consisting of three CDRs. These two sets of three CDRs may be located on the same polypeptide chain or on different polypeptide chains, thereby giving rise to different molecular architectures. Also, it is envisaged that within a given binding molecule in accordance with the present invention, a part of the binding sites is such that all six CDRs constituting a given binding site are located on a single polypeptide chain, whereas other binding sites are such that the first and second set of three CDRs constituting a given binding site are located on distinct polypeptides. Distinct polypeptides may be merely formally distinct and otherwise identical, especially as regards the amino acid sequence. Alternatively, distinct polypeptides may be distinct from each other in terms of their amino acid sequence.

The term "about" means that an acceptable error range, e.g., up to 5% or 10%, for the particular value should be assumed.

Diagnosis

The present invention further discloses methods for diagnosing and prognosing cancer.

According to an aspect, the present invention provides a diagnostic and/or prognostic method of cancer or infectious disease in a subject, the method comprises the step of determining the expression level of NKp46 in a biological sample of said subject using at least one antibody as described herein.

The term "biological sample" encompasses a variety of sample types obtained from an organism that may be used in a diagnostic or monitoring assay. The term encompasses blood and other liquid samples of biological origin, solid tissue samples, such as a biopsy specimen, or tissue cultures or cells derived there from and the progeny thereof. Additionally, the term may encompass circulating tumor or other cells. The term specifically encompasses a clinical sample, and further includes cells in cell culture, cell supernatants, cell lysates, serum, plasma, urine, amniotic fluid, biological fluids including aqueous humour and vitreous for eyes samples, and tissue samples. The term also encompasses samples that have been manipulated in any way after procurement, such as treatment with reagents, solubilization, or enrichment for certain components.

Determining the expression level of NKp46 can be performed by a labeled anti-NKp46 antibody as described herein. Determining the expression can be performed, for example, by ELISA.

The method of the invention can further comprise the step of comparing said level of expression to a control level.

The following examples are presented in order to more fully illustrate some embodiments of the invention. They should, in no way be construed as limiting the scope of the invention.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological, immunological and recombinant DNA techniques. Such techniques are well known in the art. Other general references referring to well-known procedures are provided throughout this document for the convenience of the reader.

Example 1. Nkp46 Antibody Generation and Selection

The immunogen (Nkp46-Fc) expression is made in mammalian HEK 293T cells. NKp46-Fc-fusion protein composed of the target (NKp46) protein's ectodomain and human IgG1 Fc fragment, has been produced and purified.

For immunization, BALB/c mice were injected with 50 µg of the immunogen in complete Freund's adjuvant (CFA) followed by 50 µg of the immunogen in incomplete Freund's adjuvant (IFA) at day 14 post first immunization. Next, the sera were analyzed for anti-NKp46-Fc antibody titer by ELISA. The mice with the highest titer were boosted with the 50 µg of the immunogen in PBS. After three days, the spleen of immune mice was taken and, after lysis of red blood cells, the splenocytes were fused with SP2/0 cell line. The potential hybridoma cells were seeded in 20% RPMI 1640 medium containing hypoxanthine, aminopterin, and thymidine (HAT) for selection of stable hybridoma cell lines. The abovementioned procedure was repeated five times and in total, 4600 wells were screened for anti-NKp46-Fc antibody secretion by ELISA. Then, 84 cell lines, from wells in which the supernatants were positive for the binding assay on Nkp46-Fc coated ELISA plates, were retested for their positivity. In parallel a cross-reactivity test was performed on an irrelevant Fc fusion protein. This resulted in 5 hybridoma cell lines that secreted antibodies specifically recognizing NKp46 ectodomain. Out of these antibodies, four were further selected for their IgG isotype (and not IgM isotype). All these candidates that showed the specific signal in ELISA were then subcloned and tested for their ability to recognize a native human NKp46 protein on transfectant cell lines, as described below.

Binding was initially examined on mouse thymoma BW transfectant cells expressing NKp46 (BW NKp46). As controls we used a commercially available anti-NKp46 mAb (denoted 9E2) and an anti-NKp46 mAb previously developed in our lab, 461-G1 (Arnon et al., 2004; Mandelboim et al., 2001). All antibodies tested specifically interacted with BW NKp46 but not with the parental BW cells (data not shown). To demonstrate that the antibodies recognize NKp46 naturally expressed by human NK cells, we stained IL-2 activated primary bulk human NK cells (activated NK cells). The activated NK cells used throughout the experiments were isolated from PBMCs. Our purification protocol reached approximately 97% purity and we verified their identity as CD56+CD3-cells (data not shown). Indeed, all the antibodies positively stained the activated NK cells.

Similar results were obtained with PBMCs derived from several donors (data not shown).

At this point, four different stable clonal cell lines were selected for large scale production and purification. Next, a large-scale Ab production was performed and all monoclonal antibodies were purified from the serum free medium, using GE AKTA Prime Plus Liquid Chromatography System and HiTrap Protein G columns, in an amount of few milligrams.

To identify the binding site of the anti-NKp46 mAbs, Ig-D1, Ig-D2 and Ig-NKp46 were plated at 0.1 µg/well. The plate was placed at 4° C. overnight. The next day blocking was performed (blocking buffer is PBS×1, 0.05% Tween-20, and 5% BSA) followed by addition of the mAbs at 0.1 µg/well and 10 µl/well of SN antibodies (both diluted in blocking buffer to a final volume of 100 µl). The plate was placed at 4° C. overnight. The next day, biotin anti-mouse was added (diluted in blocking buffer), followed by streptavidin-POD (diluted in blocking buffer), and with TMB for detection of samples at OD650 nm. As shown in FIG. 1, clones K3 and P4 antibodies bind to NKp46 D2 domain while clone 02, a commercial anti-NKp46, and 461-G1 (a published NKp46 antibody) bind to NKp46 D1 domain.

We next checked whether any of the anti-NKp46 mAbs could block the interaction of NKp46 with its ligands. For this, BJAB, MCF7, and C1R tumor cells which express an unknown ligand for NKp46 were used. NKp46-Ig was incubated either alone or with the various anti-NKp46 mAbs on ice. Subsequently, the incubated NKp46-Ig fusion proteins were used to FACS stain the tumor cells. None of the anti-NKp46 mAbs were able to block the binding of NKp46-Ig to the cells.

Example 2. Examination of NKp46 Downregulation from the Surface of NK Cells

Figure 2:
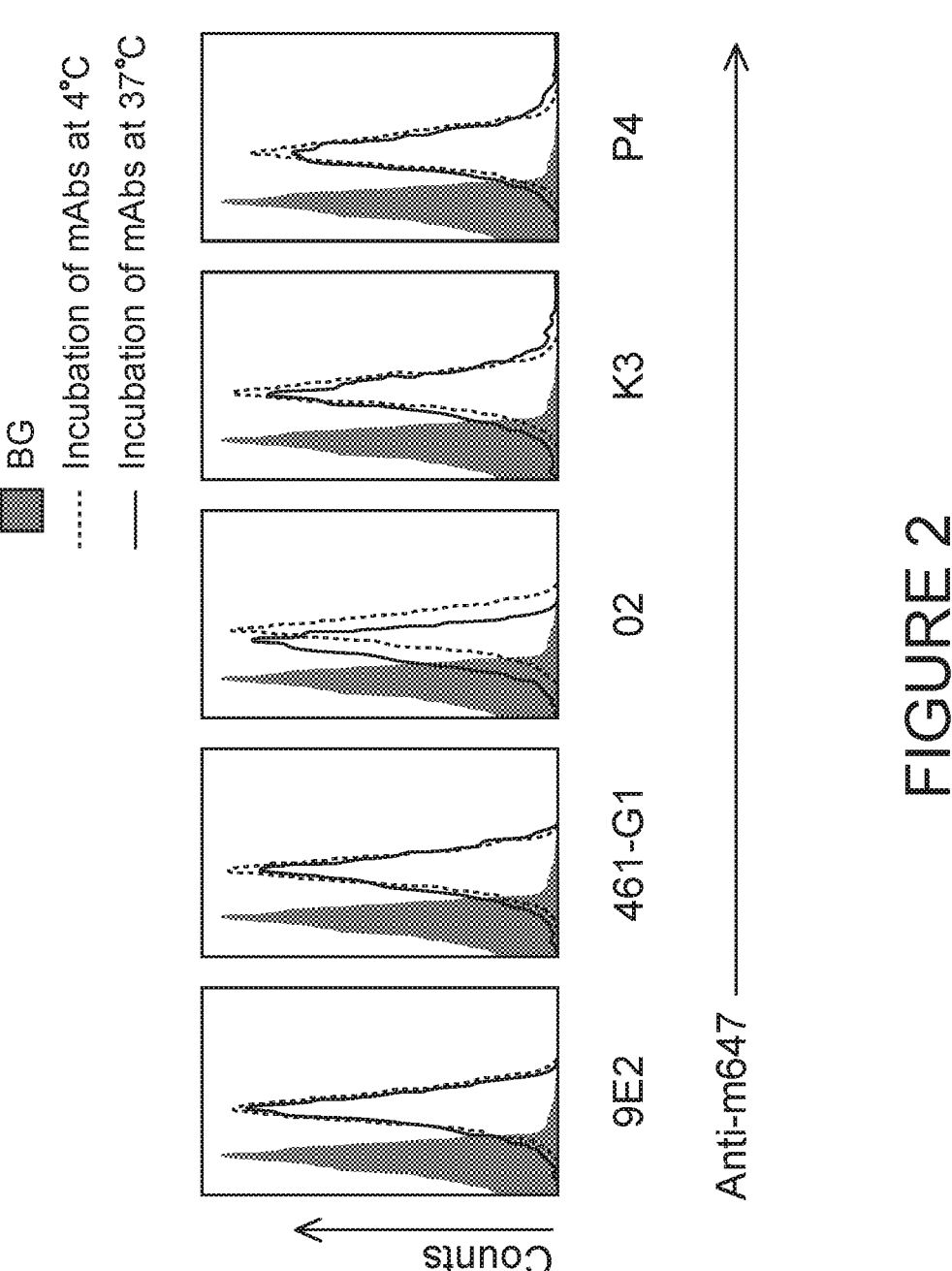
FIG. 2. Downregulation of NKp46 from the surface of NK cells. Activated bulk NK cell cultures were incubated with the indicated anti-NKp46 mAbs (9E2, 461-G1, 02, K3, P4) at 4° C. (black histogram) or at 37° C. (red histogram) for 8 hrs, followed by FACS staining with a secondary antibody (anti-m647). The filled gray histogram represents staining with secondary antibody only of cells treated at 4° C. The background of cells treated at 37° C. was similar (not shown). Figure shows one representative experiment out of 5 performed.
Figure 3:
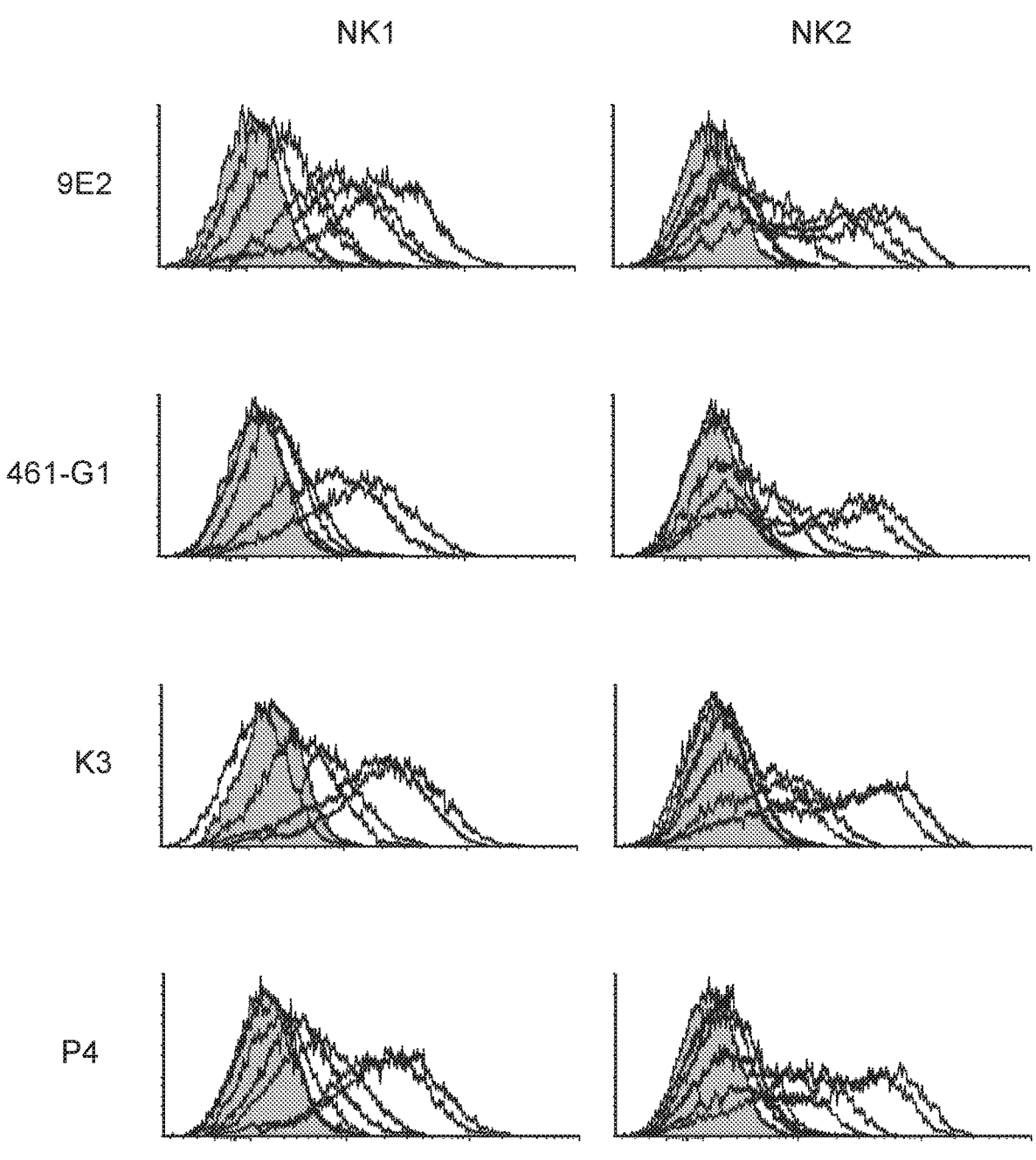
FIG. 3. Dose response of the antibodies. FACS staining using anti-NKp46 mAbs (9E2, 461-G1, K3, P4) of primary activated bulk human NK cells (colored histogram) from two donors, NK1 and NK2. The filled gray histogram represents staining of NK cells with secondary antibody only. Full grey column=Secondary ab only (m-647). Results of different concentrations of antibodies (0.5 µg, 0.1 µg, 0.05 µg, 0.01 µg, 0.005 µg, 0.001 µg, 0.005 µg, or 0.0001 µg/well are presented (higher concentration-stronger staining)).

The effect of the anti-NKp46 mAbs on the reduction of NKp46 expression on the NK cells surface was tested. The anti-NKp46 mAbs were incubated with activated NK cells for 8 hours either at 4° C. or 37° C. The cells were then FACS stained with a conjugated secondary anti-mouse antibody. Only one mAb, 02, led to reduced levels of NKp46 (FIG. 2). The other antibodies did not induce downregulation of NKp46 from the surface of NK cells. These antibodies specifically bind NKp46, and do not interfere with the binding of NKp46 to its cognate ligand. To confirm the findings, a dose response FACS staining with these antibodies was performed on two activated primary NK cells (FIG. 3). As can be appreciated, the decrease in the concentrations of K3 and P4 antibodies coincides with the decrease in the intensity of the fluorescence signal on the cell surface. Therefore, the K3 and P4 antibodies display a strong dose response and are suitable for the generation of bi- or tri-specific antibodies, which would bridge between NK cells and tumor cells.

Example 3. Humanized Anti-NKp46 Antibodies, Activity and Affinity

The parental heavy and light chain sequences of anti NKp46, clones P4 and K3 were humanized using Macromoltek software design. The sequences were confirmed by structural biology and molecular modeling experts. The resulting humanized sequences are set forth in SEQ ID No: 14 (humanization of the heavy chain of K3 and P4), SEQ ID No: 15 (humanization of the Light chain of P4), and SEQ ID No: 16 (humanization of the light chain of K3). Four humanized clones were prepared: B341001, B341002, B341003, and B341004.

The binding of the humanized antibodies with mutated IgG4 to cells expressing NKp46 was examined. The experiments were performed as follows:

1. Coat tested in a matrix of 3 conc. vs. 3 buffers to find optimal signal.
2. Optimal signal conditions were used to coat the ELISA tray, using standard blocking and washing steps.
3. Primary antibody applied in range of concentrations with 10-dilutions (MAbs with humanized variable+ mutated IgG4).
4. Secondary Ab used to detect binding was Anti-Hu Kappa with HRP (TMB substrate).
5. Absorbance measured at 450 nm.

Figure 4A:
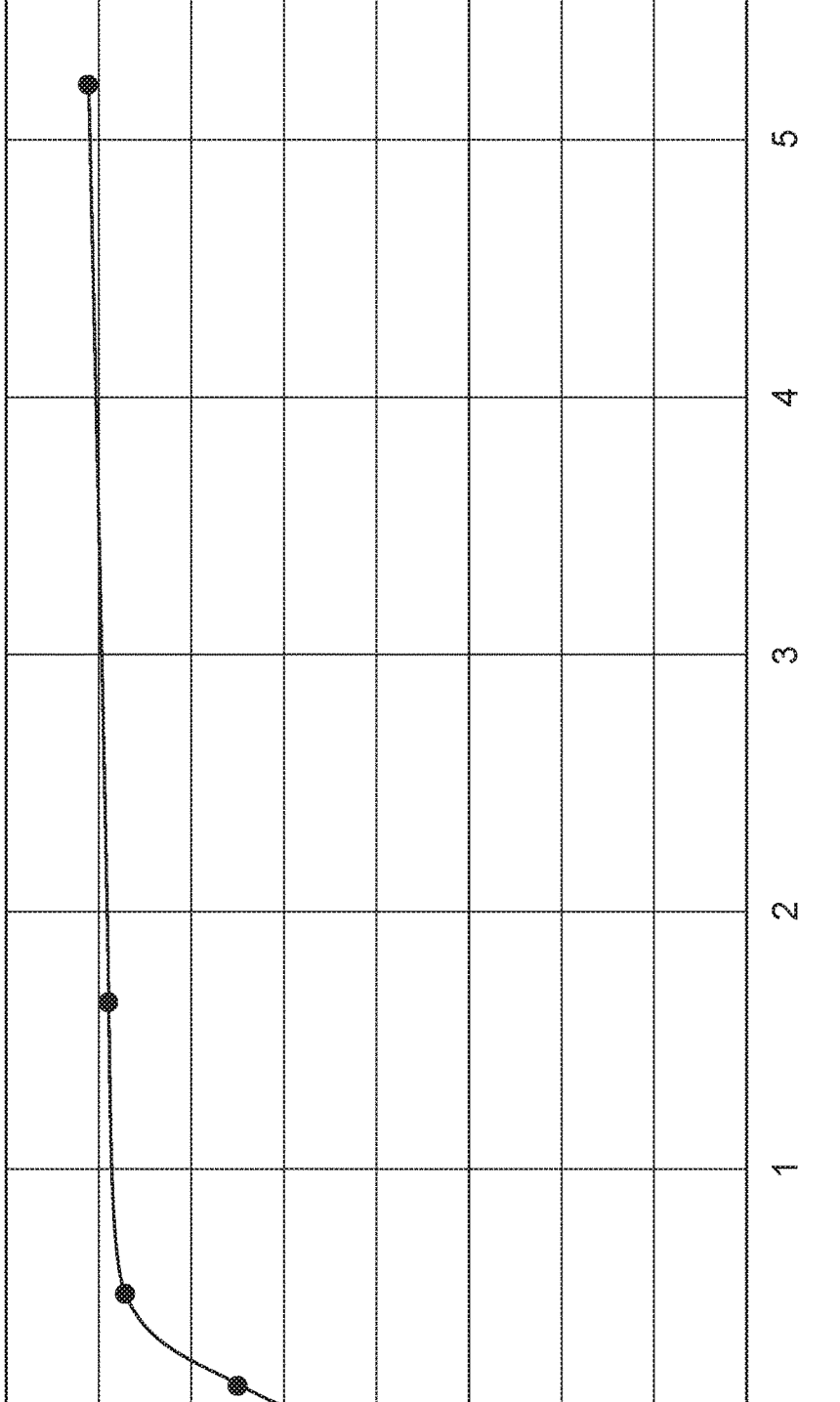
FIGS. 4A-4B. Affinity (nM) of humanized P4 (FIG. 4A) and K3 (FIG. 4B) antibodies having mutated IgG4, to NKp46.
Figure 4B:
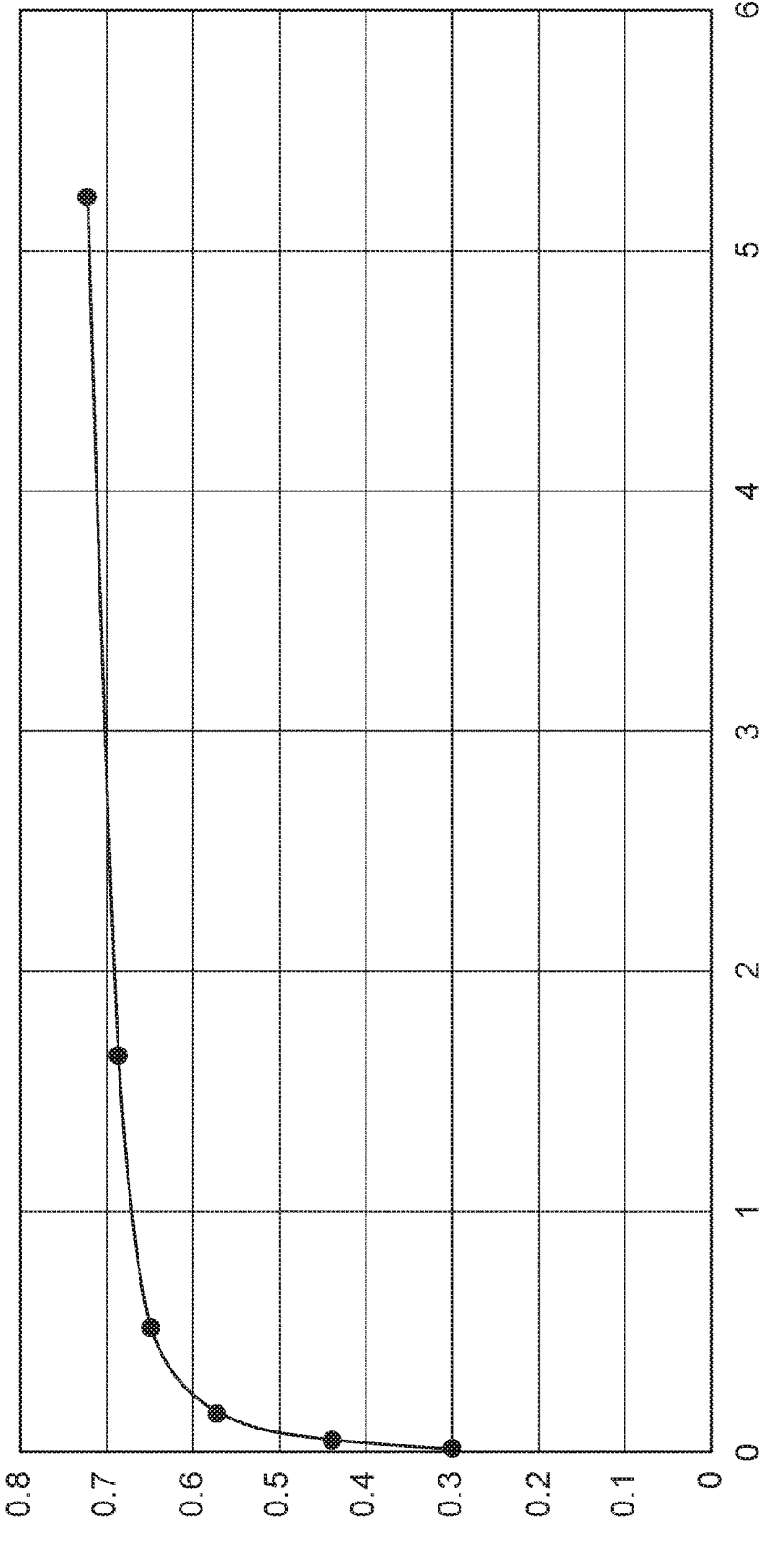

The antigen was Acro Biosystems Human NKp46 that was expressed in HEK293 cells. As shown in FIGS. 4A-4B, both humanized clones had strong affinity to NKp46 (20.5 pM and 27 pM).

The humanized antibodies were further examined for affinity to NKp46 D2 domain. As shown in FIG. 5D, the humanized antibodies exhibit an exceptionally high affinity to the D2 domain of NKp46.

Example 4. Bi and Tri Specific Antibodies

Binding molecules having two or three specificities are prepared. The bi-specific binding molecule comprises the binding site of the antibodies disclosed herein and a binding site specific to tumor ligands. The tri-specific binding molecule comprises a binding site of the antibodies described herein; a binding site to CD160; and a binding site to tumor ligands. First, for the tri-specific antibody, blocking assays against NKp46 and CD160 is performed to confirm that the antibodies do no block the receptors from binding their natural ligands. Redirected assays with antibodies clones K3 and P4 and anti-CD160 are used to show that the binding of the antibodies does no impair NK cell function.

In vivo assays are performed with SCID/Beige mice which do not express T, B or NK cells as the tumors for testing are of human origin. Establishing tumors in mice expressing the chosen tumor's antigen is performed by subcutaneously injecting increasing amounts of cancer cells ($2\times10^5$, $5\times10^5$, $1\times10^6$, $5\times10^6$). The mice are assessed every two days for the appearance of a palpable tumor, and once observed are then measured daily with a digital Vernier caliper to define tumor volume. Tumors usually appear within 10-14 days, depending on the type of tumor and amount injected. Once a palpable tumor is observed, mice are monitored for two weeks (tumor volume, weight of mice, and general appearance). The humane endpoint is set to a tumor volume of 1 cm³ or a weight loss of 20% from initial body weight. After two weeks, mice are sacrificed, the tumors are removed and weight. The ideal working number of cells is defined as: the minimal amount of cells which maintain a palpable tumor for the entire investigatory period mentioned above. Six mice per group are tested for each cell line.

Dose response experiment to determine safe amount of the bi- or tri-specific antibodies needed to reduce tumor size. Once the ideal working number of cells is determined based on the abovementioned criteria, increasing concentrations of the antibodies and the singular antibodies (K3, P4, anti-CD160, and anti-tumor antigen) are injected into SCID/Beige mice bearing tumors.

SCID/Being mice are initially injected with the determined number of cancer cells as assessed in the previous section. Once a palpable tumor appears, it is measured by a digital Vernier caliper to define tumor volume. Subsequently, the bi- or tri-specific and singular antibodies are injected i.p. at increasing doses (30 µg and 60 µg). All mice groups except for the PBS injected group are then injected also with human NK cells.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

---

The invention claimed is:

1. An antibody that binds to NKp46, or an antibody fragment thereof comprising at least an antigen binding portion, wherein the antibody or antibody fragment comprises a heavy chain (HC) complementarity determining region (CDR) 1 amino acid sequence of SEQ ID NO: 1, a HC CDR2 amino acid sequence of SEQ ID NO: 2, a HC CDR3 amino acid sequence of SEQ ID NO: 3; and a light chain (LC) CDR1 amino acid sequence of SEQ ID NO: 4, a LC CDR2 amino acid sequence of SEQ ID No: 5, and a LC CDR3 amino acid sequence of SEQ ID NO: 6.

2. The antibody or the antibody fragment according to claim 1, comprising a heavy chain variable region set forth in amino acid sequence of SEQ ID NO: 7, or an analog having at least 95% sequence similarity with said heavy chain variable region sequence.

3. The antibody or the antibody fragment according to claim 1, comprising a light chain variable sequence set forth in SEQ ID NO: 8, or an analog having at least 95% sequence similarity with said slight chain variable region sequence.

4. The antibody or the antibody fragment according to claim 1, comprising a heavy chain and a light chain, wherein the heavy chain comprises SEQ ID NO: 7 and the light chain comprises SEQ ID NO: 8.

5. The antibody fragment according to claim 1, wherein the antibody fragment is a single chain Fv (scFv).

6. The antibody or antibody fragment according to claim 1, wherein the antibody binds to human NKp46 with an affinity of $10^{-11}$ M to $10^{-16}$ M.

7. The antibody or the antibody fragment according to claim 1, wherein the antibody is a humanized antibody.

8. The antibody or the antibody fragment according to claim 7, wherein the humanized antibody comprises a heavy chain comprising SEQ ID NO: 14, and a light chain comprising a sequence selected from the group consisting of SEQ ID NOs: 15 and 16.

9. A multi-specific antibody comprising a binding site of an antibody according to claim 1.

10. The multi-specific antibody of claim 9, wherein the multi-specific antibody is a bi-specific antibody further comprising a binding site having specificity to a tumor antigen.

11. The multi-specific antibody of claim 9, wherein the multi-specific antibody is a bi-specific antibody further comprising a binding site having specificity to a viral, bacterial, or fungal antigen.

12. The multi-specific antibody of claim 9, wherein the multi-specific antibody is a tri-specific antibody further comprising a binding site specific to CD160 or CD16.

13. The multi-specific antibody of claim 9, wherein the multi-specific antibody is fused or conjugated to a cytokine.

14. A pharmaceutical composition comprising as an active ingredient, at least one antibody or fragment thereof according to claim 1, and a pharmaceutical acceptable excipient, diluent, salt, or carrier.

15. A method of treating cancer, comprising administering to a subject in need thereof, a pharmaceutical composition according to claim 14.

16. A method of treating an infection in a subject, comprising administering a pharmaceutical composition according to claim 15 to a subject in need thereof.

17. A chimeric antigen receptor (CAR) comprising at least one antibody or antibody fragment according to claim 1.

18. A method of treating cancer comprising administering to a subject in need thereof, at least one cell expressing the CAR according to claim 17.

* * * * *

SEQUENCE LISTING

```
<160> NUMBER OF SEQ ID NOS: 16

<210> SEQ ID NO 1
<211> LENGTH: 5
<212> TYPE: PRT
<213> ORGANISM: Mus musculus

<400> SEQUENCE: 1

Glu Tyr Ser Met His
1               5

<210> SEQ ID NO 2
<211> LENGTH: 17
<212> TYPE: PRT
<213> ORGANISM: Mus musculus

<400> SEQUENCE: 2

Gly Ile Ser Pro Asn Ser Gly Gly Thr Ser Tyr Asn Gln Lys Phe Lys
1               5                   10                  15

Gly

<210> SEQ ID NO 3
<211> LENGTH: 9
<212> TYPE: PRT
<213> ORGANISM: Mus musculus

<400> SEQUENCE: 3

Arg Asp Phe His Ser Ser Phe Asp Tyr
1               5

<210> SEQ ID NO 4
<211> LENGTH: 11
<212> TYPE: PRT
<213> ORGANISM: Mus musculus

<400> SEQUENCE: 4

Arg Ala Ser Gln Ser Ile Ser Asp Tyr Leu His
1               5                   10

<210> SEQ ID NO 5
<211> LENGTH: 7
<212> TYPE: PRT
<213> ORGANISM: Mus musculus

<400> SEQUENCE: 5

Tyr Ala Ser Gln Ser Ile Ser
1               5

<210> SEQ ID NO 6
<211> LENGTH: 9
<212> TYPE: PRT
<213> ORGANISM: Mus musculus

<400> SEQUENCE: 6
```

```
Gln Asn Gly His Ser Phe Pro Leu Thr
1               5

<210> SEQ ID NO 7
<211> LENGTH: 118
<212> TYPE: PRT
<213> ORGANISM: Mus musculus

<400> SEQUENCE: 7

Glu Val Gln Leu Gln Gln Ser Gly Pro Glu Leu Val Lys Pro Gly Thr
1               5                   10                  15

Ser Val Lys Ile Ser Cys Lys Thr Ser Gly Tyr Thr Phe Thr Glu Tyr
            20                  25                  30

Ser Met His Trp Val Lys Gln Ser His Gly Lys Ser Leu Glu Trp Phe
        35                  40                  45

Gly Gly Ile Ser Pro Asn Ser Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Asp Phe His Ser Ser Phe Asp Tyr Trp Gly Gln Gly Thr
            100                 105                 110

Thr Leu Thr Val Ser Ser
        115

<210> SEQ ID NO 8
<211> LENGTH: 107
<212> TYPE: PRT
<213> ORGANISM: Mus musculus

<400> SEQUENCE: 8

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Phe Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Pro Gly Thr Lys Leu Glu Leu Lys
            100                 105

<210> SEQ ID NO 9
<211> LENGTH: 354
<212> TYPE: DNA
<213> ORGANISM: Mus musculus

<400> SEQUENCE: 9
gaggtccagc tgcaacagtc tggacctgaa ctggtgaagc ctgggacttc agtgaagata      60
tcctgcaaga cttctggata cacattcact gaatacagca tgcactgggt gaagcagagc     120
catggaaaga gccttgagtg gtttggaggt attagtccta cagtggtgg taccagctac     180
```

```
aaccagaagt tcaagggcaa ggccacattg actgtagaca agtcctccag cacagcctac        240
atggagctcc gcagcctgac atctgaggat tctgcagtct attactgtgc acgaagggac        300
ttccatagta gctttgacta ctggggccaa ggcaccactc tcacagtctc ctca             354

<210> SEQ ID NO 10
<211> LENGTH: 321
<212> TYPE: DNA
<213> ORGANISM: Mus musculus

<400> SEQUENCE: 10
gacattgtga tgactcagtc tccagccacc ctgtctgtga ctccaggaga tagagtctct         60
ctctcctgca gggccagcca gagtattagc gactacttac attggtttca acaaaaatca        120
catgagtctc caaggcttct catcaaatat gcttcccaat ccatctctgg gatcccctcc        180
aggttcagtg gcagtggatc agggtcagat ttcactctca gtatcaacag tgtggaacct        240
gaagatgttg gagtgtatta ctgtcaaaat ggtcacagct ttccgctcac gttcggtcct        300
gggaccaagc tggagctgaa a                                                   321

<210> SEQ ID NO 11
<211> LENGTH: 321
<212> TYPE: DNA
<213> ORGANISM: Mus musculus

<400> SEQUENCE: 11
gatattgtcc taactcagtc tccagccacc ctgtctgtga ctccaggaaa tagcgtcagt         60
ctttcctgca gggccagcca aagtattagc gactacttac attggtttca acaaaaatca        120
catgagtctc caaggcttct catcaaatat gcttcccaat ccatctctgg gatcccctcc        180
aggttcagtg gcagtggatc agggtcagat ttcactctca gtatcaacag tgtggaacct        240
gaagatgttg gagtgtatta ctgtcaaaat ggtcacagct ttccgctcac gttcggtcct        300
gggaccaagc tggagctgaa a                                                   321

<210> SEQ ID NO 12
<211> LENGTH: 107
<212> TYPE: PRT
<213> ORGANISM: Mus musculus

<400> SEQUENCE: 12

Asp Ile Val Leu Thr Gln Ser Pro Ala Thr Leu Ser Val Thr Pro Gly
1               5                   10                  15

Asn Ser Val Ser Leu Ser Cys Arg Ala Ser Gln Ser Ile Ser Asp Tyr
            20                  25                  30

Leu His Trp Phe Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Pro Gly Thr Lys Leu Glu Leu Lys
            100                 105

<210> SEQ ID NO 13
<211> LENGTH: 134
<212> TYPE: PRT
```

```
<213> ORGANISM: Homo sapiens

<400> SEQUENCE: 13

Tyr Asp Thr Pro Thr Leu Ser Val His Pro Gly Pro Glu Val Ile Ser
1               5                   10                  15

Gly Glu Lys Val Thr Phe Tyr Cys Arg Leu Asp Thr Ala Thr Ser Met
            20                  25                  30

Phe Leu Leu Leu Lys Glu Gly Arg Ser Ser His Val Gln Arg Gly Tyr
        35                  40                  45

Gly Lys Val Gln Ala Glu Phe Pro Leu Gly Pro Val Thr Thr Ala His
    50                  55                  60

Arg Gly Thr Tyr Arg Cys Phe Gly Ser Tyr Asn Asn His Ala Trp Ser
65                  70                  75                  80

Phe Pro Ser Glu Pro Val Lys Leu Leu Val Thr Gly Asp Ile Glu Asn
                85                  90                  95

Thr Ser Leu Ala Pro Glu Asp Pro Thr Phe Pro Ala Asp Thr Trp Gly
            100                 105                 110

Thr Tyr Leu Leu Thr Thr Glu Thr Gly Leu Gln Lys Asp His Ala Leu
        115                 120                 125

Trp Asp His Thr Ala Gln
    130

<210> SEQ ID NO 14
<211> LENGTH: 118
<212> TYPE: PRT
<213> ORGANISM: Artificial sequence
<220> FEATURE:
<223> OTHER INFORMATION: Humanized antibody

<400> SEQUENCE: 14

Glu Val Gln Leu Gln Gln Ser Gly Ala Glu Val Lys Lys Pro Gly Ser
1               5                   10                  15

Ser Val Lys Val Ser Cys Lys Thr Ser Gly Tyr Thr Phe Thr Glu Tyr
            20                  25                  30

Ser Met His Trp Val Arg Gln Ala Pro Gly Lys Ser Leu Glu Trp Phe
        35                  40                  45

Gly Gly Ile Ser Pro Asn Ser Gly Gly Thr Ser Tyr Asn Gln Lys Phe
    50                  55                  60

Lys Gly Arg Ala Thr Leu Thr Val Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asp Phe His Ser Ser Phe Asp Tyr Trp Gly Gln Gly Thr
            100                 105                 110

Thr Val Thr Val Ser Ser
        115

<210> SEQ ID NO 15
<211> LENGTH: 107
<212> TYPE: PRT
<213> ORGANISM: Artificial sequence
<220> FEATURE:
<223> OTHER INFORMATION: Humanized antibody

<400> SEQUENCE: 15

Asp Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp Tyr
```

-continued

```
                20                    25                    30

Leu His Trp Phe Gln Gln Lys Pro His Glu Ser Pro Arg Leu Leu Ile
        35                    40                    45

Lys Tyr Ala Ser Gln Ser Ile Ser Gly Ile Pro Ala Arg Phe Ser Gly
    50                    55                    60

Ser Gly Ser Gly Ser Asp Phe Thr Leu Thr Ile Ser Ser Leu Glu Pro
65                    70                    75                    80

Glu Asp Phe Ala Val Tyr Tyr Cys Gln Asn Gly His Ser Phe Pro Leu
                85                    90                    95

Thr Phe Gly Pro Gly Thr Lys Val Asp Ile Lys
                100                   105

<210> SEQ ID NO 16
<211> LENGTH: 118
<212> TYPE: PRT
<213> ORGANISM: Artificial sequence
<220> FEATURE:
<223> OTHER INFORMATION: Humanized antibody

<400> SEQUENCE: 16

Asp Ile Val Leu Thr Gln Ser Pro Ala Thr Leu Ser Leu Ser Pro Gly
1               5                    10                    15

Glu Arg Ala Thr Leu Ser Cys Arg Ala Ser Gln Ser Ile Ser Asp Tyr
                20                    25                    30

Leu His Trp Phe Gln Gln Lys Pro His Glu Ser Pro Arg Leu Leu Ile
        35                    40                    45

Lys Tyr Ala Ser Gln Ser Ile Ser Gly Ile Pro Ala Arg Phe Ser Gly
    50                    55                    60

Ser Gly Ser Gly Ser Asp Phe Thr Leu Thr Ile Ser Ser Leu Glu Pro
65                    70                    75                    80

Glu Asp Phe Ala Val Tyr Tyr Cys Gln Asn Gly His Ser Phe Pro Leu
                85                    90                    95

Thr Phe Gly Pro Gly Thr Lys Val Asp Ile Lys Arg Thr Val Ala Ala
                100                   105                   110

Pro Ser Val Phe Ile Phe
            115
```